(12) United States Patent
Beal

(10) Patent No.: US 11,209,419 B2
(45) Date of Patent: Dec. 28, 2021

(54) LIFECYCLE ASSESSMENT SYSTEMS AND METHODS FOR DETERMINING EMISSIONS FROM ANIMAL PRODUCTION

(71) Applicant: Low Carbon Beef, LLC, Glencoe, OK (US)

(72) Inventor: Colin M. Beal, Glencoe, OK (US)

(*) Notice: Subject to any disclaimer, the term of this patent is extended or adjusted under 35 U.S.C. 154(b) by 0 days.

(21) Appl. No.: 17/098,415

(22) Filed: Nov. 15, 2020

(65) Prior Publication Data
US 2021/0148891 A1    May 20, 2021

Related U.S. Application Data

(60) Provisional application No. 62/935,774, filed on Nov. 15, 2019.

(51) Int. Cl.
*G01N 33/497* (2006.01)
*G01N 33/00* (2006.01)
(Continued)

(52) U.S. Cl.
CPC ....... *G01N 33/497* (2013.01); *G01N 33/0031* (2013.01); *G01N 33/0062* (2013.01);
(Continued)

(58) Field of Classification Search
CPC ......... Y02E 50/10; Y02E 50/30; Y02E 20/18; Y02E 50/12; Y02E 50/14; Y02E 50/16; Y02E 50/343; Y02P 30/20; Y02P 20/151; Y02P 60/14; Y02P 60/21; Y02P 90/84; Y02P 20/143; Y02P 20/145; Y02P 40/121; Y02P 60/20; Y02P 90/845; Y02P 30/40;
(Continued)

(56) References Cited

U.S. PATENT DOCUMENTS

2009/0326715 A1* 12/2009 Liska ............... G06Q 10/10
                                                           700/266
2011/0192213 A1*  8/2011 Zimmerman ....... A01K 5/02
                                                            73/23.3
(Continued)

FOREIGN PATENT DOCUMENTS

WO   2015099313 A1   7/2015
WO   2019175666 A2   9/2019

OTHER PUBLICATIONS

Alcock et al. Can animal genetics and flock management be used to reduce greenhouse gas emissions but also maintain productivity of wool-producing enterprises? (2017) Agricultural systems. vol. 132, pp. 25-34. (Year: 2017).*

(Continued)

*Primary Examiner* — Mary K Zeman
(74) *Attorney, Agent, or Firm* — Shah IP Law, PLLC

(57) ABSTRACT

Approaches provide for machine learning or training algorithms that apply modifications to models based on a type of data obtained, including, for example, producer-specific management practice data, genetic data, among other such data. The animal-centric models can be configured to, for example, quantify gas emissions (e.g., greenhouse gas emissions) that an animal may be expected to emit over a period of time, including, for example, over the animal's lifetime. The emissions in certain embodiments can further enable the certification of emissions for individual animals.

16 Claims, 11 Drawing Sheets

(51) Int. Cl.
  *G16B 20/00*   (2019.01)
  *G06F 30/27*   (2020.01)
  *G16B 5/00*    (2019.01)
  *G16B 40/00*   (2019.01)

(52) U.S. Cl.
  CPC .............. *G16B 20/00* (2019.02); *G06F 30/27* (2020.01); *G16B 5/00* (2019.02); *G16B 40/00* (2019.02)

(58) Field of Classification Search
  CPC .. Y02P 60/30; G06Q 10/06393; G06Q 50/02; G06Q 10/06; G06Q 50/00; G06Q 10/04; G06Q 10/063; G06Q 10/0639; G06Q 30/018; G06Q 10/08; G06Q 99/00; G06T 11/206; G06T 11/20; G06T 15/20; A23K 10/30; A23K 10/10; A23K 10/14; A23K 40/00; A23K 50/10; Y02C 20/40; Y02C 10/06; Y02C 10/14; Y02C 10/02; Y02C 10/04; Y02C 10/08; Y02C 10/12; G01C 21/3469; G06F 2119/08; G06F 2219/10; G06F 30/20; G06F 30/27; G06F 11/3006; G06F 11/3051; G06F 16/29; G06F 16/9535; G06F 17/10; G06F 21/566; G06F 17/11; G06F 3/00; G06F 16/00; G06F 16/212; G06F 16/2465; G06F 16/248; G06F 16/9024; G06F 21/6218; G06F 2216/03; G06N 20/00; G06N 5/04; G06N 5/02; G06N 3/08; G06N 20/10; G06N 20/20; G06N 5/003; G06N 7/005; G06N 7/023; C10L 5/445; Y02A 40/20; Y02A 50/20; Y02A 40/25; Y02W 30/50; Y02W 90/00; C12P 5/023; C12P 7/08; C01B 32/50; C01B 2203/1241; G16B 50/00; G16B 15/00; G16B 40/00; G16B 20/00; G16B 5/00; G16B 10/00; G16B 5/20; G16B 30/10; G16B 40/10; G01N 33/497; G05B 13/04; G05B 13/048; G05B 13/042; G16H 50/20; G16H 40/63; G16H 10/40; G16H 40/67; G16H 15/00; G16H 50/30; G16H 10/60; G16H 20/60; G16H 50/50; G16H 50/70
  See application file for complete search history.

(56) References Cited

U.S. PATENT DOCUMENTS

| | | | |
|---|---|---|---|
| 2012/0023000 A1* | 1/2012 | Rhodes, III | G06Q 10/06 705/37 |
| 2012/0271677 A1* | 10/2012 | Rhodes, III | G06Q 10/06 705/7.27 |
| 2014/0229119 A1 | 8/2014 | Van Der Kamp et al. | |
| 2019/0259108 A1* | 8/2019 | Bongartz | A01G 7/045 |
| 2020/0184153 A1* | 6/2020 | Bongartz | G06N 5/04 |
| 2021/0007330 A1* | 1/2021 | Huisma | G06Q 10/06315 |

OTHER PUBLICATIONS

Mosnier et al. ORFEE: a bio-economic model to simulate integrated and intensive management of mixed-crop livestock farms and their greenhouse gas emissions. (2017) vol. 157 p. 202-215. (Year: 2017).*

Chobtang, J. et al Environmental trade-offs associated with intensification methods in a pasture-based dairy system using prospective attributional life cycle assessment. (2017) Journal of Cleaner Production, vol. 143, p. 1302-1312, and supplemental data, 28 pages. (Year: 2017).*

Herrero, M. et al. Biomass use, production, feed efficiencies and greenhouse gass emissions from global livestock systems. (2013) PNAS vol. 110, No. 52 p. 20888-20893. (Year: 2013).*

Hyland, J.J. et al. Improving livestock production efficiencies presents a major opportunity to reduce sectoral greenhouse gas emissions. (2016) vol. 147 p. 123-131. (Year: 2016).*

Cederberg, C. An LCA researcher's wish list—data and emission models needed to improve LCA studies of animal production. (2013) Animal, 7S2 p. 212-219. (Year: 2013).*

McClelland, S.C. et al. Type and number of environmental impact categories used in livestock life cycle assessment: a systematic review (2018) Livestock Science vol. 209, p. 39-45. (Year: 2018).*

Van Middelaar, C.E. Methods to determine the relative value of genetic traits in dairy cows to reduce greenhouse gas emissions along the chain. (2014) J Dairy Science, vol. 97, 5191-5205. (Year: 2014).*

Rice, p. Evaluation of allocation methods for calculation of carbon footprint of grass-based dairy production. (2017) Journal of environmental management vol. 202, p. 311-319 and supplemental. (Year: 2017).*

Rotz, C.A. Symposium review: modeling greenhouse gas emissions from dairy farms. (2018) J Dairy Science vol. 101, p. 6675-6690. (Year: 2018).*

Veltman, K. et al. Comparison of process-based models to quantify nutrient flows and greenhouse gas emissions associated with milk production. (2017) Agriculture Ecosystems and Environment vol. 237, p. 31-44 and supplemental. (Year: 2017).*

Bell (2011) Modelling the effects of genetic line and feeding system on methane emissions from dairy systems. Thesis, PhD The Univ of Edinburgh. 156 pages. (Year: 2011).*

Boaity (2017) Three Essays on Beef Genomics: economic and environmental impacts. Thesis, PhD, University of Alberta. 378 pages. (Year: 2017).*

Gulzari et al. Combining models to estimate the impacts of future climate scenarios on feed supply, greenhouse gas emissions and economic performance on dairy farms in Norway. 2017 Agricultural systems, vol. 157 p. 157-169. (Year: 2017).*

Hayes (2016) Genomic heritabilities and genomic estimated breeding values for methane traits in Angus cattle, Journal of Animal Science, vol. 94, Issue 3, Mar. 2016, pp. 902-908. (Year: 2016).*

VanderHaar et al. (2015) Harnessing the genetics of the modern dairy cow to continue improvements in feed efficiency. J Dairy Science. 99:4941-4954. (Year: 2015).*

Dehaas et al. (2011) Genetic parameters for predicted methane production and potential for reducing enteric emissions through genomic selection. J Dairy Science 94:6122-6134. (Year: 2011).*

International Application No. PCT/US2020/060640, Search Report and Written Opinion dated Feb. 25, 2021, (9 pages).

* cited by examiner

LIFECYCLE ASSESSMENT SYSTEMS AND METHODS FOR DETERMINING EMISSIONS FROM ANIMAL PRODUCTION

CROSS-REFERENCE TO RELATED APPLICATIONS

The present application claims priority to U.S. provisional application No. 62/935,774, filed Nov. 15, 2019, and entitled "LIFECYCLE ASSESSMENT SYSTEMS AND METHODS FOR DETERMINING ANIMAL GREENHOUSE GAS EMISSIONS," which is hereby incorporated herein in its entirety for all purposes.

BACKGROUND

As the global population increases and people desire more animal protein, beef demand is expected to rise, which is expected to result in the rise of beef production. While beef provides many nutritional benefits, beef cattle can generate greenhouse gas (GHG) emissions. These emissions can be generated from a variety of sources within the beef production lifecycle, including enteric methane production, methane and nitrous oxide from manure, direct on-farm emissions (such as diesel combustion in tractors), and embedded upstream emissions generated during the production of feeds, seeds, fertilizers, etc. imported into the system. Meanwhile, as stated by some sources, global temperatures and atmospheric GHG concentrations continue to increase, raising concerns for some people about the negative impact of future climate changes on global society. As a result, there are sustainability initiatives aimed at reducing GHG emissions from segments of the economy, including, for example, transportation segment, electricity segment, industry segment, buildings segment, and agriculture segment.

Conventional lifecycle assessment (LCA) protocols have been developed for quantifying the environmental performance of a variety of beef production systems. However, many of these protocols provide performance results at the global, national, or aggregate producer level, without enabling the resolution to evaluate (and certify) individual animal performance. As a result, some of these protocols have had limited practical market application and consumers have been unable to differentiate beef produced with low GHG emissions from beef produced through conventional means with higher emissions.

SUMMARY

Systems and methods in accordance with various embodiments describe model optimization techniques. In particular, various approaches describe machine learning or training algorithms that apply modifications to models based on a type of data obtained, including, for example, producer-specific management practice data, performance data, among other such data. The animal-centric models can be configured to, for example, quantify emissions that an animal may be expected to emit over a period of time, including, for example, over the animal's lifetime. In an embodiment, emissions can include emissions of any substance that can impact the environment, including but not limited to, greenhouse gas emissions such as $CO_2$, $CH_4$, $N_2O$, etc.; pollutants such as particulate matter, NOx, SOx, etc.; substances contributing to eutrophication and nutrients such as N, P, K, etc.; ozone depleting substances such as CFCs, etc.; toxicity substances such as herbicides, pesticides, anti-microbials, etc.; ionizing radiation such as U235, etc.; etc. The emissions data in certain embodiments can further enable the certification of emissions for individual animals.

In an embodiment, data for use in determining gas emissions can be obtained. The data may include, for example, farm practices management data, historic emissions and expected emissions data, expected progeny performance data, genomics data, phenotypic data, and/or animal performance data. The data may be identified, extracted, and/or determined from a variety of different disaggregated sources.

For example, expected progeny performance data of animals can be used to estimate gas emissions (herein referred to as "emissions") for select animals. Expected progeny performance data provides estimates of the genetic value of an animal as a parent. Essentially, differences in expected progeny performance data between animals of the same species may be used to predict differences in performance between their future offspring when each is mated to animals of the same average genetic merit. Various embodiments leverage expected progeny performance data to determine the emissions over an assessment cycle.

Genomic data can be used to, for example, determine the animal's genetic disposition to traits that influence emissions over an assessment cycle (e.g., feed efficiency, growth, etc.). The genomic data generally refers to part of, or all of, an animal's sequenced genome including portions of the genome sometimes referred to as genetic markers, genetic sequences, single nucleotide polymorphisms (i.e., SNPs), DNA, DNA blocks, genes, or nucleotides. Genomic data may be used, alone or in combination with one or more other data and/or equations described herein to determine an animal's emissions or expected emissions over an assessment cycle.

Phenotypic data can be used to, for example, determine emissions over an assessment cycle. Phenotypic data generally refers to an animal's observable characteristics and production characteristics that can be measured, including, but not limited to: 1) measurements of body parts (e.g., meat, bone, hide, feet/hooves, feathers, head, leg, wing, muscles, udder, scrotum, etc.) or the whole body for heights, weights, lengths, colors, etc.; 2) measurements of body parts, the whole body, animal products (e.g., carcass, organs, tallow, milk, etc.), or waste products (e.g., manure, gases, shells, etc.) for composition data related to elements and compounds (C, N, P, $CH_4$, $N_2O$, etc.), biological components (proteins, amino acids, lipids, fatty acids, carbohydrates, water, etc.), economically valuable components (e.g., meat, bone, hide, prime cuts, omega-3 fatty acids, etc.), etc.; 3) measurements of body parts, the whole body, animal products, or waste products for yields of animal products (e.g., eggs, milk, meat, cheese, blood, fat, protein, manure, etc.), 4) measurements of body parts, the whole body, animal products, or waste products for yields of other biological or chemical data (e.g., rumen condition, milk somatic cell count, antibodies, etc.); 5) animal performance data (e.g., behavior, docility, dry matter intake, energy intake, feed conversion efficiency, growth rate, water intake, reproduction/pregnancy rates, manure production, oocyte production, embryo production, etc.); 6) other measurable data related to livestock production. An animal's measured phenotypic data may be used, alone or in combination with one or more other data and/or equations described herein, to determine an animal's emissions or expected emissions over an assessment cycle.

Farm practices and/or farm management practices/protocol data can be used to, for example, determine emissions over an assessment cycle. Farm practices management data refers to a variety of different data sources, including, but not limited to: feeds, fertilizers, manure management, grazing management, on farm energy use, water supply (fresh water usage), etc. A farm's management practice data/protocols may be used, alone or in combination with one or more other data and/or equations described herein, to determine an animal's emissions or expected emissions over an assessment cycle.

In certain embodiments, the data can be obtained using one or more sensors. For example, sensors can be used to monitor automatically and continuously the consumption, emissions, and the behavior of animals. The data can be used to predict and determine a variety of conditions relating to health, performance, and production efficiency enabling determination of individual animal performance on different rations, response to medications, response to feed supplements, response to minerals and trace minerals, response to growth promoting substances, prediction of carcass quality, and determination of greenhouse gas and manure excretion.

Once the data is obtained, a unique model (e.g., an animal-centric or animal that utilizes the animal data can be generated. For example, input parameters of the model can be dynamically selected based on available data. In an example, one or more input parameters can be added or removed or otherwise selected based on the presence (or absence) of farm practices management data, historic emissions and expected emissions data, expected progeny performance data, genomics data, phenotypic data, and/or obtained animal performance data. In short, the model can be dynamically updated based on available data, including updating the input parameters or weighting of those input parameters. Thereafter, the model can be used to determine emissions data for each animal or group of animals. Specifically, embodiments described herein generate a unique model based on livestock performance data, progeny performance data, genetics data, phenotypic data, and/or farm practices management data to determine an animal's emissions. For example, the data may be aggregated, and/or determined to generate a rating that is indicative of the amount of emissions an animal may have emitted or may be expected to emit over its lifetime. The rating system may be used to inform consumers about greenhouse gas emissions that are associated with their consumption of animal products. Moreover, the rating system may be used by farm managers to raise animals in a more sustainable fashion to reduce the amount of greenhouse gas emissions that are associated with raising and cultivating animals. Indeed, the ratings and/or some of the calculated output may be used to help farm managers make better decisions about farm practices to reduce greenhouse gas emissions.

Embodiments described herein primarily reference cattle. However, various embodiments may be applied to other livestock, including, but not limited to poultry, swine, equine, etc. without departing from the scope of the embodiments described herein.

Embodiments described herein primarily reference greenhouse gas emissions. However, various embodiments may be applied to other emissions, including, but not limited to pollutants, emissions causing eutrophication, ozone depleting substances, ionizing radiation, etc. without departing from the scope of the embodiments described herein.

Embodiments provide a variety of advantages. For example, in accordance with various embodiments, with conventional approaches consumers do not have access to information regarding the production emissions of the beef and other animal products available for purchase. By providing emissions data for pieces of beef and other animal products, consumers have the information necessary to make socially-conscious purchasing decisions.

In addition, giving consumers more information regarding the emissions associated with individual animal products for purchase, various embodiments provide emissions information about the farms where the beef or other animals were raised. This enhances consumer knowledge of emissions and allows the consumer to make informed purchasing decisions.

Additionally, various embodiments provide greater information about an animal to farmers. Farmers analyze livestock performance data and expected progeny performance data carefully when making breeding decisions or selecting which animals to purchase. Currently, livestock performance data and expected progeny performance data do not contain emissions data for individual animals. By providing emissions data for individual animals, farmers will have more information to use when making breeding decisions or when selecting which animals to purchase.

Another benefit in accordance with various embodiments is that approaches described herein encourage sustainable practices. Farmers that use this information to produce animals with low emissions will mitigate emissions, and thereby institute more sustainable practices on their land and through the entire supply chain. Such sustainable practices include using less fertilizer, being more thoughtful about water allocation and use, using feeds that generate lower emissions, and reducing emissions from transport and retail storage.

Various other functions and advantages are described and suggested below as may be provided in accordance with the various embodiments.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1A:
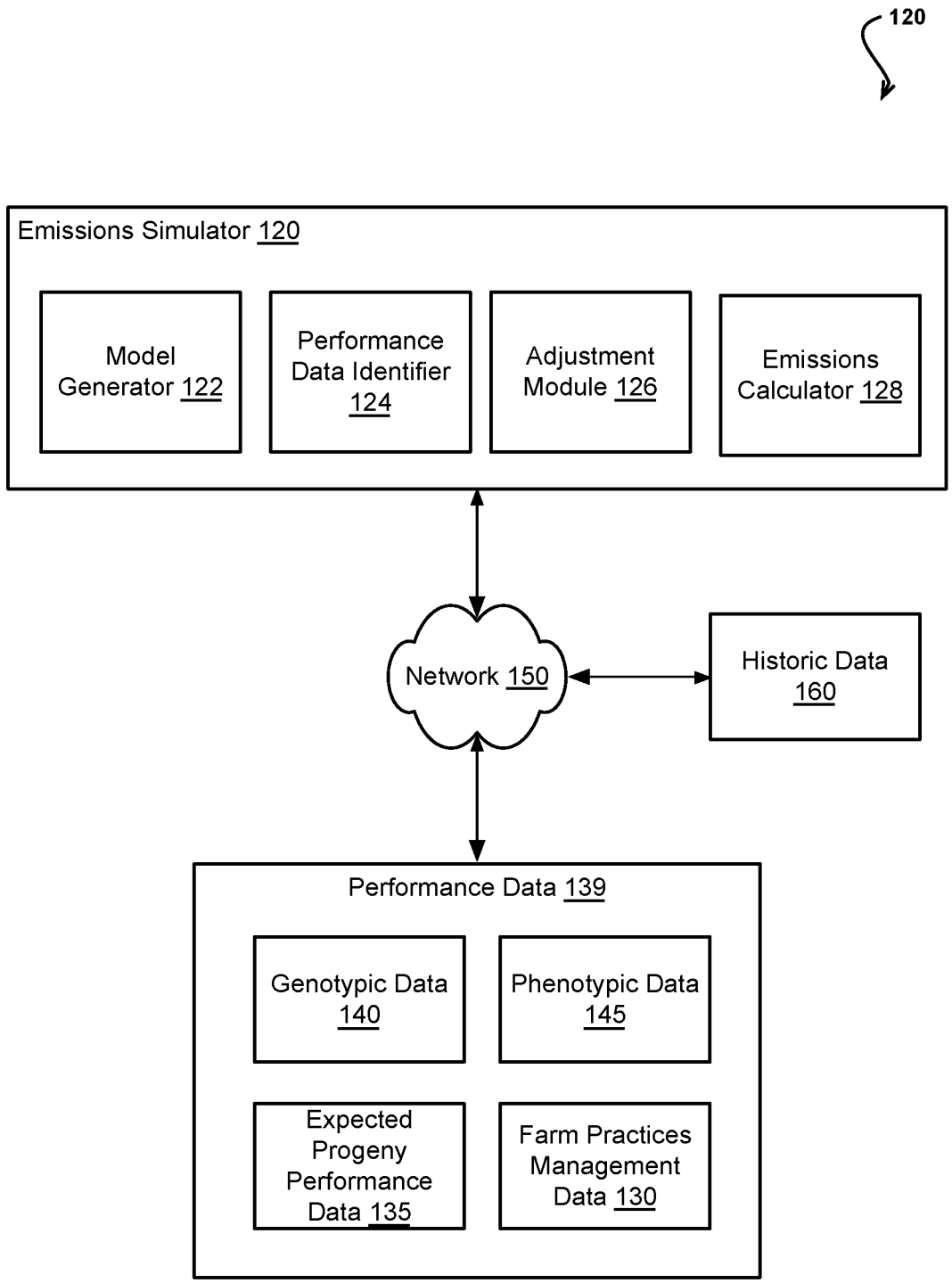
FIG. 1A illustrates a system for utilizing performance data of animals to estimate emissions for selected animals in accordance with various embodiments.

The inventive system and method (hereinafter sometimes referred to more simply as "system" or "method") described herein uses performance data (hereinafter, performance data may more generally refer to historic data, expected progeny performance data, genomic data, phenotypic data, and/or farm practices management data) to trigger modifications to models based on a type of data obtained, where the model(s) can be used to determine estimated emissions for one or more animals. More succinctly, embodiments described herein describe systems and methods for measuring and tracking emissions by an animal through the whole animal life cycle using dynamically updating models. The system is a computer program product which collects information about selected animals, and generates a model that utilizes the animal data and facilitates adjustments based on related variables, and then determines emissions data for each animal or group of animals. Specifically, various embodiments uniquely model a variety of performance data to determine an animal's emissions. It also may certify an animal based on its' own genomics and/or its' own performances. Approaches described herein can also adjust for farm management protocols in its model to determine specific farm emission rates.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step).

Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

The figures described herein generally illustrate an example approaches to estimating emissions for selected animals in accordance with various embodiments. It should be understood that reference numbers are carried over between figures for similar components for purposes of simplicity of explanation, but such usage should not be construed as a limitation on the various embodiments unless otherwise stated. It should be further noted that emissions can be emissions (i.e., discharge) of any substance that can impact the environment, including but not limited to greenhouse gas emissions such as CO2, CH4, N2O, etc.; pollutants such as particulate matter, NOx, SOx, etc.; eutrophication and nutrients such as N, P, K, etc.; ozone depleting substances such as CFCs, etc.; toxicity substances such as herbicides, pesticides, anti-microbials, etc.; ironizing radiation such as U235, etc.; etc. Reference to an animal or a group of animals as cattle is merely an example, and embodiments described herein apply to any number of different types of animals.

FIG. 1A illustrates a system for utilizing performance data of animals to estimate emissions for selected animals in accordance with various embodiments. The system is comprised of historic data 160, farm practices management data 130, expected progeny performance data 135, genotypic data 140, phenotypic data 145, emissions simulator 120, and a network 150 over which the various systems communicate and interact. Emissions simulator 120 is described in greater detail in FIG. 2. Below, however, generally, emission simulator 120 generates a model that determines emissions.

As illustrated in FIG. 1A, the emissions simulator 120 may be comprised of model generator 122, performance data identifier 124, adjustment module 126, and emissions calculator 128. The various computing devices described herein are exemplary and for illustration purposes only. The system may be reorganized or consolidated, as understood by a person of ordinary skill in the art, to perform the same tasks on one or more other servers or computing devices without departing from the scope of embodiments described herein.

In an exemplary embodiment, the emissions simulator 120 obtains input parameters from historic data 160. Emissions simulator 120 generates a model, which includes equation components based on input parameters that model the impact of certain characteristics on an animal's lifecycle emissions. Emissions simulator 120 obtains performance data 139, which may be comprised of progeny performance data 135, genotypic data 140, phenotypic data 145, and farm practices management data 130, and identifies performance data variables (e.g., expected progeny performance data variables, genotypic data variables, phenotypic data variables, farm practices management data variables) that may affect emissions. Emissions simulator 120 can apply adjustments to the model equations based on the performance data. The adjustments can be with respect to baseline emissions. For example, the adjustments can be with respect to baseline emissions for a particular breed of animal. Specifically, the emissions simulator can determine emissions output by an animal by applying the adjusted model equations to obtain model output.

Historic data 160 includes input parameters that impact emissions. The historic data may be compiled from academic papers, scientific literature, lifecycle assessment inventory databases, trade publications, experimental data, etc. In one embodiment, the relevant papers may specifically study the effects of various input parameters on emissions. In the same or other embodiments, the relevant papers may study animal characteristics data that may or may not specifically analyze or study animal characteristic data and its direct impact on emissions. For example, the historic data 160 may be comprised of information about different parts of an animal lifecycle, including, but not limited to performance data 139, emissions information, economic impact information, etc.

In one embodiment, the historic data 160 may be comprised of, for example, dry matter intake (DMI) data.

In one embodiment, the historic data 160 may be comprised of, for example, data from publications such as reports and papers from the IPCC, FAO, ecoInvent, scientific literature, or trade organizations.

In one embodiment, historic data 160 may be comprised of, for example, data from reports and textbooks including: International Organization for Standardization (ISO iso.org); 2006 IPCC Guidelines for National Greenhouse Gas Inventories (and subsequent updates); FAO Tackling Climate Change Through Livestock report; Inventory of US Greenhouse Gas Emissions and Sinks, U.S. EPA, 2018; 2019 Sustainability Report, Tyson Foods, 2020; Parker D. et al., Agricultural energy consumption, biomass generation, Texas A&M, 1997; Field T. and Taylor R., Scientific Farm Animal Production, 2020; etc.

In an embodiment, the historic data 160 may be comprised of, for example, data 5 from lifecycle assessment inventories including: Wernet, G., Bauer, C., Steubing, B., Reinhard, J., Moreno-Ruiz, E., and Weidema, B., 2016, the ecoinvent database version 3 (part I): overview and methodology, the International Journal of Life Cycle Assessment, [online] 21(9), pp.1218-1230.

In one embodiment, historic data 160 may be comprised of, for example, scientific journal articles including: Capper J., Is the Grass Always Greener? Comparing the Environmental Impact of Conventional, Natural and Grass-Fed Beef Production Systems, Animals, 2012; Beauchemin K. et al., Life cycle assessment of greenhouse gas emissions from beef production in western Canada: A case study, Agricultural Systems, 2010; Stanley P. et al., Impacts of soil carbon sequestration, Agricultural Systems, 2018; Machado L., Effects of marine and freshwater macroalgae on in vitro total gas and methane production, PLOS One, 2014; Pelletier N., Environmental performance in the US broiler poultry sector: Life cycle energy use and greenhouse gas, ozone depleting, acidifying and eutrophying emissions, Agricultural Systems, 2008; Verge X. et al., Greenhouse gas emissions from the Canadian pork industry, Livestock Science, 2009; Parker R. et al., Fuel use and greenhouse gas emissions of world fisheries, Nature Climate Change, 2018; etc.

In one embodiment, historic data 160 may be comprised of, for example, data from ration calculators including: Lalman D., OSU Cowculator v2.0 Beef Cow Nutrition Evaluation Software, Oklahoma State University, 2020; U of M Feedlot Ration Balancer, The University of Minnesota, 2008; Analysis & Ingredient Management, CFCTech, 2020; Swine Ration Calculator, North Carolina State University, 2000; Nates S., Aquafeed Formulation, 2015; etc.

In one embodiment, historic data 160 may be comprised of, for example, data from commercial products including: Purina 4-square Breeder Cubes, Product Label; NatureWise Meatbird 22% Crumble, Nutrena, Product Label; Producer's Pride, Hog Feed Pellets, Product Label; Bayer Environmental Science, Cimarron Max, Product Label; etc.

In one embodiment, historic data 160 may be comprised of, for example, data from industry websites including: lowcarbonranch.com, cattlefax.com, angus.org, hereford.org, drovers.com, ncba.org, nppc.org, americandairy.com, apppa.org, etc.

In one embodiment, historic data 160 may be comprised of, for example, data from experimental data including: Lopez, A., Soil Test Report, Soil No. 13983, Water, and Forage Analytical Laboratory, Oklahoma State University, 2019; Beal C., Forage Analysis Report No. 12768, Soil, Water, and Forage Analytical Laboratory, Oklahoma State University, 2019; Closeout Report, Payment Summary, Lot ID 20167210, Creekstone Farms Premium Beef LLC, Jun.

17, 2020; Robinson C., Beal_Data Report OSU Feedlot Willard Sparks.xlsx, Weights and Feed Report, Oklahoma State University, 2020; Martin B., Personal Communication, Beal C., 2018; etc.

In one embodiment, the historic data 160 may be comprised of human and/or machine-readable information that may be processed, as described in more detail below, to perform additional analysis.

Model generator 122, which is described in more detail below in reference to the emissions simulator 120, may be comprised of model equations that may be derived from historic data 160. In one embodiment, the model generator 122 models the impact of various historic data 160 characteristics on emissions. This can include modeling a baseline impact on emissions for available historic data. For example, the model generator 122 may model how DMI affects emissions output by an animal. The model equations may be generated based on historic data 160 in one instance, and/or may be based on a variety of different studies and/or practical correlations that may or may not be present in the historic data 160. In one embodiment, the model equations generated by the model generator 122 may be comprised of historic data 160, farm practices management data 130, genotypic data 140, phenotypic data 145, expected progeny performance data 135, that may be received from one or more other database/sources.

Expected progeny performance data 135 may be comprised of information about expected performance of an animal's offspring. In one embodiment, expected progeny performance data 135 may be comprised of, for example, data from: NeoGen, Zoetis, SeeDNA, iQBirdTesting, Angus Genetics Inc., Method Genetics, another third party, etc.; Academic organizations such as Oklahoma State University Animal Science Department, Texas A&M AgriLife, Iowa State University Extension and Outreach, etc.; Consultants such as veterinarians, geneticists, scientists, and others skilled in the art; blockchain databases; etc. Specifically, expected progeny performance data 135 for cattle may include expected progeny performance data or expected progeny differences (EPDs), e.g., expected birth weight, expected weaning weight, expected dry matter intake, expected milk production, expected mature weight, expected carcass weight, etc. Expected progeny performance data 135 may be received from a variety of different sources and proprietary databases, or may be generated based on genotypic and/or phenotypic data. One or more model equations can be generated, identified, selected, etc., based on the expected progeny performance data.

In another example, genotypic data 140 may be comprised of genomic information about an animal. In one embodiment, genomic data 140 may be comprised of, for example, data from: personal communication with animal owner, feedlot owner, animal product processing facility, meat packing facility, retail staff, etc.; NeoGen, Zoetis, SeeDNA, iQBirdTesting, Angus Genetics Inc., Method Genetics, another third party, etc.; Academic organizations such as Oklahoma State University Animal Science Department, Texas A&M AgriLife, Iowa State University Extension and Outreach, etc.; Consultants such as veterinarians, geneticists, scientists, and others skilled in the art; blockchain databases; etc. The genetic information may inform a variety of data and/or assumptions about an animal's emissions expectations. For example, certain genetic markers may be correlated to greater or lower carcass weight and/or greater or lower dry matter intake, etc. In one embodiment, the genotypic data 140 may be incorporated into expected progeny performance data 135. One or more model equations can be generated, identified, selected, etc., based on genotypic data.

In yet another example, phenotypic data 145 may be comprised of one or more animal's observable characteristics, including height, weight, composition, feed efficiency, etc. as described above. In one embodiment, phenotypic data 140 may be comprised of, for example, data from: personal communication with animal owner, feedlot owner, animal product processing facility, meat packing facility, retail staff, etc. such as Abernathy Ranches, Hy-Plains Feedyard, Tyson Foods, Meyer Natural Foods LLC, Walmart, etc.; Breed association such as American Angus Association, American Hereford Association, etc.; Phenotypic database such as animal owner records, American Angus Association's National Sire Evaluation, International Dairy Food Association, etc.; Animal management software such as CattleMax, HerdOne, Layer Farm Manager, Dairy Wellness, PigCHAMP, etc.; Consultants such as veterinarians, geneticists, scientists, and others skilled in the art; blockchain databases; etc. The phenotypic data 145 may inform a variety of data and/or assumptions about an animal's emissions expectations, which may be incorporated by the model generator 122. For example, certain phenotypic characteristics may be correlated to greater or lower dry matter intake, etc. In one embodiment, the phenotypic data 145 may be incorporated into expected progeny performance data 135. One or more model equations can be generated, identified, selected, etc., based on phenotypic data.

In another example, farm practices management data 130 may be comprised of data obtained and/or collected from a farm. For example, in one embodiment, farm practices management data 130 may be comprised of, for example, data from: personal communication with animal owner, feedlot owner, animal product processing facility, meat packing facility, retail staff, etc.; Third party certifications such as Oregon Tilth, BeefTraxx, IMI Global, etc.; Government agencies such as USDA, EPA, etc.; Academic organizations such as Oklahoma State University Animal Science Department, Texas A&M AgriLife, Iowa State University Extension and Outreach, etc.; Consultants such as veterinarians, geneticists, scientists, and others skilled in the art; blockchain databases; etc. Farm practices management data 130 may be comprised of, among other things, feeds, fertilizers, manure management, grazing management, on farm energy use, water supply (fresh water usage), etc. Certain farm practices management data 130 may be correlated to greater or lower greenhouse gas emissions. One or more model equations can be generated, identified, selected, etc., based on farm practice management data.

Performance data identifier 124 identifies performance data variables from performance data 139 that may affect emissions determination. In one embodiment, identifying performance data variables may include, for example, utilizing internal protocols and training modules; Consultants such as veterinarians, geneticists, scientists, engineers, lifecycle assessment experts, and others skilled in the art. In an embodiment, utilizing one or more sources described herein, for example, expected dry matter intake and/or expected carcass weight, which may be obtained from expected progeny performance data 135, may be identified as affecting the emissions calculations—and, as such, may be identified by the performance data identifier 124.

The emissions simulator 120 may take the data and resulting model equations into account in its model generator 122 to determine emissions emitted by one or more animals on a particular farm or collection of animal production facilities. In an embodiment, one or more of a plurality of approaches can be used to generate the model including, for example, practitioner formulations, regression analysis, statistical analysis, sensitivity analysis, Monte Carlo simulation, experimental trials, artificial intelligence, machine learning, training algorithms, etc.

Adjustment module 126 allows for adjustments to the model equations based on performance data variables (e.g., from identified performance data 139. That is, adjustment module 126 generates adjustment parameters accounting for differences with respect to different sets of performance data 139 and historic data 160. For example, the adjustments can be with respect to baseline emissions for a particular breed of animal or particular farm management practices. In one exemplary embodiment, the adjustment module 126 applies scaling factors, thresholds, and/or multipliers to model equations to ensure that an appropriate emissions determination is obtained based on performance data. The amount and nature of the adjustments may be determined by the performance data and/or the data point's likely impact on the determined expected emissions values. Generally, the adjustments may be determined based on historical performance data 160 and/or in real time or near real time. Additionally, in another exemplary embodiment of the adjustment module 126, thresholds may be applied to the model equations (i.e., positive or negative). In one embodiment, emissions simulator 120 may generate a baseline scenario and subsequent operations might adjust model 126 components for one or more additional scenarios to compare respective emissions. In one embodiment, adjustments to model components may include, for example, utilizing expert practitioner formulations, regression analysis, statistical analysis, sensitivity analysis, Monte Carlo simulation, experimental trials, artificial intelligence, machine learning, training algorithms, etc.

Emissions calculator 128 determines the expected emissions by applying adjusted modeling equations to obtain model output. In one exemplary embodiment, emissions calculator 128 determines expected emissions by applying a simulation to create expected probability distributions. More simply, the simulation iteratively runs the emissions calculator 128 to determine the range of possible emissions and the likelihood of the actual value being within the range. One exemplary simulation to determine expected emissions values may be a Monte Carlo simulation wherein the inputs are randomized and many simulations are run in order to determine the probabilities of different outcomes. Other simulations may be used as would be apparent to one skilled in the art. In one embodiment, determining expected emissions may include, for example, utilizing lifecycle Assessment (LCA), Integrated Assessment Modeling (IAM), Environmental Impact Assessment (EIA), etc. including methods related to allocation by mass, energy, economic value, etc., system expansion, displacement credits, offsets, any number of accounting methods, any number of pre-determined frameworks and systems such as ReCiPe End Point, ReCiPe Midpoint, TRACI, SimaPro, OpenLCA, Brightway LCA, GREET, CIVIL, eco-indicator 99, ecological footprint, EPID2003, IMPACT 2002+, USETox, Land Use Change, Indirect Land Use Change, ecosystem quality, climate change, human health, cumulative energy demand, fossil energy demand, etc.

A variety of different outputs may be determined by the emissions calculator 128, including, but not limited to values for: carbon dioxide equivalent emissions ($CO_2e$) absorbed on farm credit, respiratory $CO_2e$ emissions, manure $CO_2e$ emissions, $CO_2e$ emissions from enteric $CH_4$, $CO_2e$ emissions upstream (upstream emissions are emissions that occur outside of the production process, but are "embedded" in energy or materials that are used in the production process), $CO_2e$ emissions from manure $N_2O$, $CO_2e$ directly emitted on farm, $CO_2e$ emissions from soil $N_2O$, $CO_2e$ emissions from manure $CH_4$, $CO_2e$ sequestered in soil or other media, $CO_2e$ sequestration flows, and other greenhouse gas fluxes. In various embodiments, the units of emissions outputs may include, for example, kg $CO_2e$/kg carcass weight, kg $CO_2e$/kg live weight, kg $CO_2e$/animal, t $CO_2e$/lb meat, kg $CO_2e$/egg, kg $CO_2e$/gallon milk, kg $CO_2e$/kg protein, kg $CO_2e$/calorie, kg $CO_2e$/\$ economic value, points of environmental impact per any given yield, moles of H+eq, kg 2-4-d eq, kg N, kg $CO_2e$, kg CFC 11 eq, kg $NO_x$ eq, various combinations of units, etc.

Network cloud 150 generally represents a network or collection of networks (such as the Internet or a corporate intranet, or a combination of both) over which the various components illustrated in FIG. 1A (including other components that may be necessary to execute the system described herein, as would be readily understood to a person of ordinary skill in the art). In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network 150 or a combination of two or more such networks 150. One or more links connect the systems and databases described herein to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable network 150, and any suitable link for connecting the various systems and databases described herein.

The network 150 connects the various systems and computing devices described or referenced herein. In particular embodiments, network 150 is an intranet, an extranet, a virtual private network (VPN), a local area network (LAN), a wireless LAN (WLAN), a wide area network (WAN), a metropolitan area network (MAN), a portion of the Internet, or another network or a combination of two or more such networks 150. The present disclosure contemplates any suitable network 150.

One or more links couple one or more systems, engines or devices to the network 150. In particular embodiments, one or more links each includes one or more wired, wireless, or optical links. In particular embodiments, one or more links each includes an intranet, an extranet, a VPN, a LAN, a WLAN, a WAN, a MAN, a portion of the Internet, or another link or a combination of two or more such links. The present disclosure contemplates any suitable links coupling one or more systems, engines or devices to the network 150.

In particular embodiments, each system or engine may be a unitary server or may be a distributed server spanning multiple computers or multiple datacenters. Systems, engines, or modules may be of various types, such as, for example and without limitation, web server, news server, mail server, message server, advertising server, file server, application server, exchange server, database server, or proxy server. In particular embodiments, each system, engine or module may include hardware, software, or embedded logic components or a combination of two or more such components for carrying out the appropriate functionalities implemented or supported by their respective servers. For example, a web server is generally capable of hosting websites containing web pages or particular elements of web pages. More specifically, a web server may host HTML files or other file types, or may dynamically create or constitute files upon a request, and communicate them to clients' devices or other devices in response to HTTP or other requests from clients' devices or other devices. A mail server is generally capable of providing electronic mail services to various clients' devices or other devices. A database server is generally capable of providing an interface for managing data stored in one or more data stores.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiment, each data storage may be a relational database. Particular embodiments may provide interfaces that enable servers or clients to manage, e.g., retrieve, modify, add, or delete, the information stored in data storage.

The system may also contain other subsystems and databases, which are not illustrated in FIG. 1A, but would be readily apparent to a person of ordinary skill in the art. For example, the system may include databases for storing data, storing features, storing outcomes (training sets), and storing models. Other databases and systems may be added or subtracted, as would be readily understood by a person of ordinary skill in the art, without departing from the scope of the embodiments described herein.

Figure 1B:
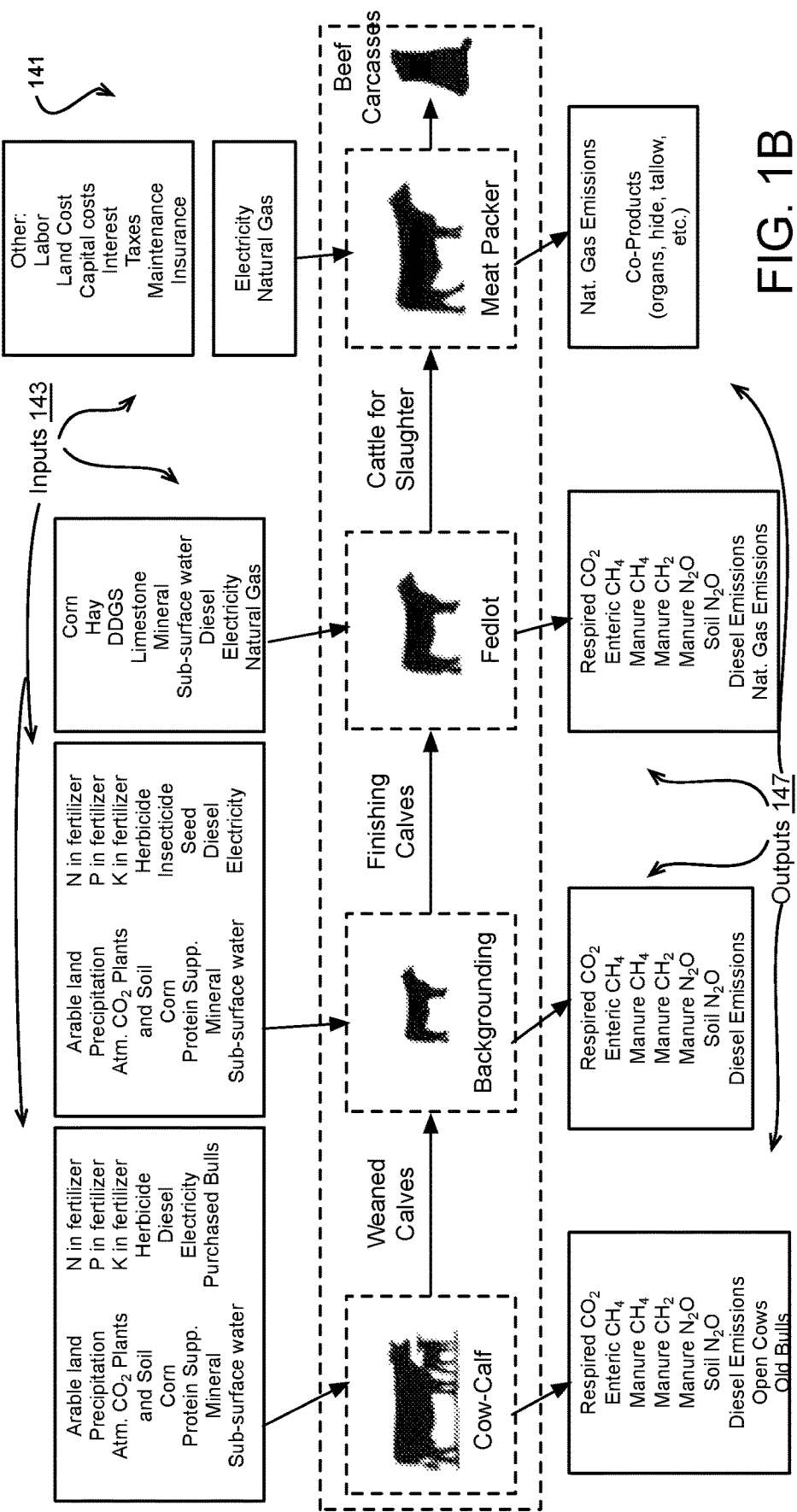
FIG. 1B illustrates an example production system in accordance with various embodiments.

FIG. 1B illustrates an example production system in accordance with various embodiments. Production system 141 can be used to represent the lifecycles (e.g., cow-calf, backgrounding, feedlot, meat packer, etc.) or parts of the lifecycles of animals being evaluated for emissions output. For example, the lifecycles can be associated with input data and output data as represented in FIG. 1B. Input 143 is associated with input parameters that impact emissions as illustrated by outputs 147. Output 147 may be comprised of greenhouse gas fluxes, product yields, or other metrics, such as one or more of the following: total lifecycle $CO_2e$ emissions, $CO_2e$ emissions for part of the lifecycle, $CO_2e$ absorbed on farm credit, respiratory $CO_2e$ emissions, manure $CO_2e$ emissions, $CO_2e$ emissions from enteric $CH_4$, $CO_2e$ emissions upstream, $CO_2e$ emissions from manure $N_2O$, $CO_2e$ emissions direct on farm, $CO_2e$ emissions from soil $N_2O$, $CO_2e$ emissions from manure $CH_4$, $CO_2e$ sequestered in soil, $CO_2e$ credits, negative $CO_2e$ emissions, $CO_2e$ sequestration fluxes, carcass weight yield, by-product yields, manure yield, etc. The model may also output different combinations of emissions (e.g., emissions from feedlot only) or the model may output the total emissions for the entire pathway, total methane, and/or total $N_2O$, etc. As used herein, upstream emissions refer to emissions that occur outside of the beef production process, but are "embedded" in energy or materials that are used in the beef production process. Examples include nitrogen fertilizer production: ammonia is produced from natural gas and air offsite and that process causes emissions—but those emissions are attributed to the beef once the farmer purchases the nitrogen fertilizer and uses it on their farm. The same approach can be used for other materials and energy that is imported into the control volume, including, for example, feeds, fuels, seeds, etc. Although the aforementioned model outputs are detailed herein, other model outputs may be generated as would be apparent to one skilled in the art.

Model equations can characterize the production system with equations representing, for example, cow-calf models, backgrounding models, feedlot models, meat packing models, operations models, etc. The model equations can provide performance results at, for example, global, national, aggregate producer level, groups of animals, or individual animals. As will be described further in FIG. 2, a model based on the model equations can be dynamically updated based on available data. For example, adjustments can be applied to the model equations based on performance data. The adjustments can be with respect to baseline emissions as determined by, for example, inputs 143 associated with production system 141. For example, the adjustments can be with respect to baseline emissions for a particular breed of animal associated with a particular production system. In one embodiment, updating the model may include, for example, utilizing expert practitioner formulations, regression analysis, statistical analysis, sensitivity analysis, Monte Carlo simulation, experimental trials, artificial intelligence, machine learning, training algorithms, etc.

Figure 2:
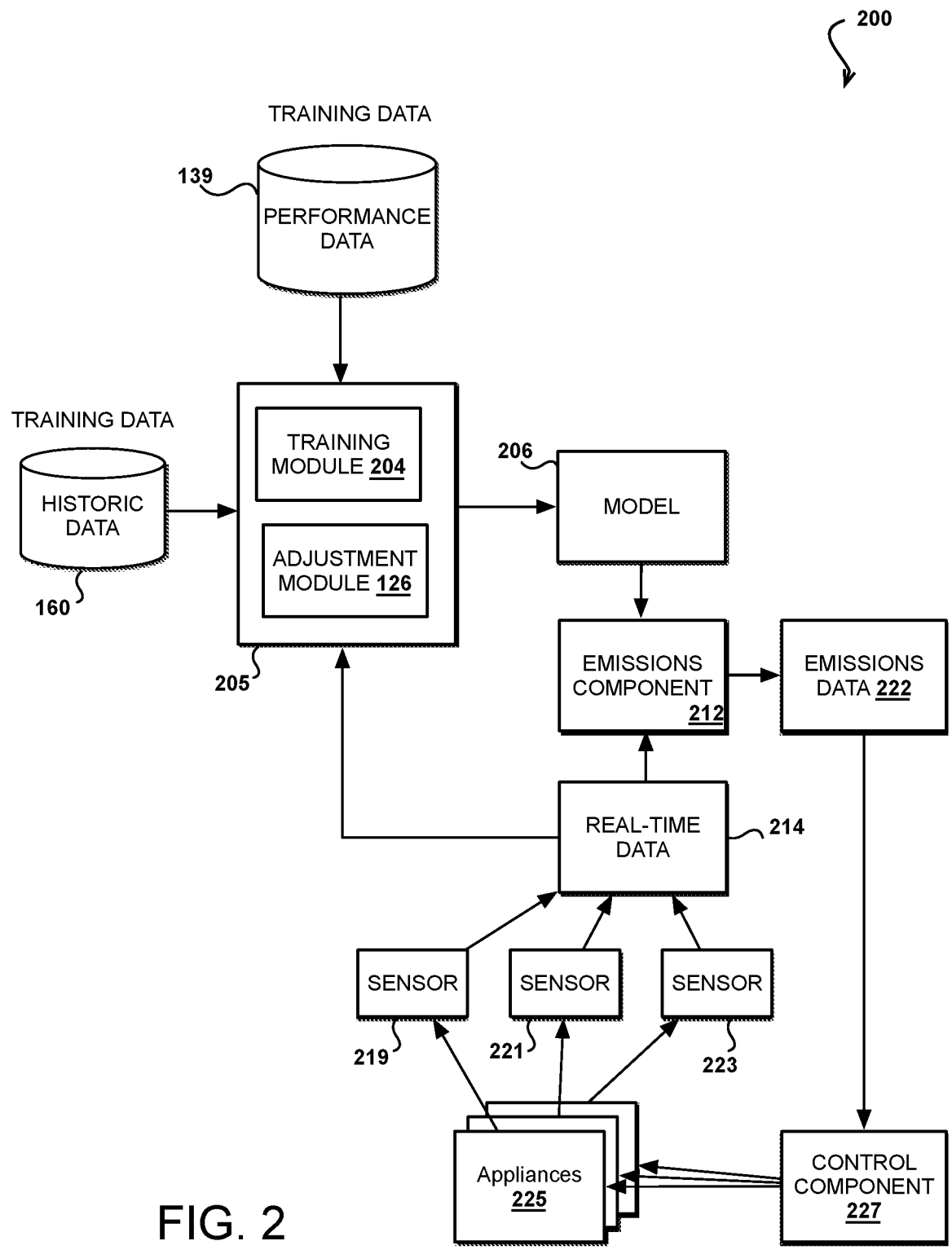
FIG. 2 illustrates an example model training pipeline that can be utilized in accordance with various embodiments.

As described, a model can be dynamically updated based on available data. Example 200 of FIG. 2 illustrates an example pipeline that can be utilized in accordance with various embodiments. In this example, historic data 160 and performance data 139 are obtained and can be used to generate model 206. Model 206 can be used to determine estimated emissions for one or more animals. The model can include one or more equation components. The equation components of the model can be based on input parameters that model the impact of certain characteristics on an animal's lifecycle emissions.

For example, historic data 160 can be used to determine input parameters that impact emissions. The historic data may be compiled from academic papers, scientific literature, trade publications, etc. For example, the historic data may be comprised of information about different parts of animal lifecycle, including, for example, emissions information, economic impact information, etc. More specifically, historic data may include data grass-fed feedlot inputs including arable land data, precipitation data, atmospheric $CO_2$ data, etc. Performance data 139 can include, for example, expected progeny performance data, genotypic data, phenotypic data, and farm practices management data.

In this example, historic data 160 and performance data 139 are accessible to training and adjustment component 205 that includes training module 204 and adjustment module 126. Training module 204 and adjustment module 126 are illustrated within the training and adjustment component 205 for illustration purposes. They may reside inside or outside training and adjustment component 205, as would be readily understood to a person of ordinary skill in the art. Training module 204 can provide the data to model 206. In some examples, model 206 directly obtains the data and/or obtains the data via one or components and/or processes. Model 206 can include, for example, equation components based on input parameters that models the impact of certain characteristics on an animal's lifecycle emissions. For example, a model may be comprised of model equations that may be derived from historic data 160 and performance data 139.

MODEL EXAMPLES

Models can be generated to represent the lifecycles or parts of the lifecycles of animals being evaluated. For example, the greenhouse gas emissions for a livestock system can be represented as the sum of the emissions from each part within that system, which can be represented by:

$$GHG[CO2e] = \sum_i^n GHG_i \quad \text{EQ 1}$$

As an example, for beef production, model equations can include, for example, equations associated with greenhouse gas fluxes as follows. Photosynthesis can be represented by:

$$GHG_p\left[\frac{\text{kg CO}_2e}{\text{yr}}\right] = -\sum\left(DMI\left[\frac{\text{kg}}{\text{yr}}\right] \cdot CC_p\left[\frac{\text{kg C}}{\text{kg}}\right]\right) \cdot CF\left[\frac{\text{kg CO}_2}{\text{kg C}}\right] \quad \text{EQ 2}$$

where DMI is the total dry matter intake of each material, $CC_p$ is the carbon content of each material, and CF is the CO2 conversion factor (44/12). Respiration can be represented by:

$$GHG_r\left[\frac{\text{kg CO}_2e}{\text{yr}}\right] = DMI\left[\frac{\text{kg DM}}{\text{yr}}\right] \cdot RF\left[\frac{\text{kg CO}_2}{\text{kg DM}}\right] \quad \text{EQ 3}$$

where RF is the respiration factor based on data from literature. $CO_2$ emitted from manure ($GHG_{mco2}$) is calculated for pasture and feedlot settings as:

$$GHG_{mco2}\left[\frac{\text{kg CO}_2e}{\text{yr}}\right] = VS\left[\frac{\text{kg}}{\text{yr}}\right] \cdot CC_m\left[\frac{\text{kg C}}{\text{kg}}\right] \cdot CF\left[\frac{\text{kg CO}_2}{\text{kg C}}\right] \quad \text{EQ 4}$$

where $CC_m$ is the carbon content of the manure volatile solids (VS). Manure $CH_4$ emissions ($GHG_{mch4}$) are calculated according to the IPCC as:

$$GHG_{mch4}\left[\frac{\text{kg CO}_2e}{\text{yr}}\right] = VS\left[\frac{\text{kg}}{\text{yr}}\right] \cdot B_o\left[\frac{\text{kg CH}_4}{\text{kg}}\right] \cdot 0.67 \cdot MCF[-] \cdot GWP_{CH_4}\left[\frac{\text{kg CO}_2e}{\text{kg CH}_4}\right] \quad \text{EQ 5}$$

where $B_O$ is the maximum $CH_4$ capacity, MCF is the methane conversion factor and $GWP_{CH_4}$ is the global warming potential for methane. Manure $N_2O$ emissions ($GHG_{mn2o}$) are calculated as the sum of direct ($GHG_{mn2oD}$), indirect volatile ($GHG_{mn2oV}$), and indirect leaching ($GHG_{mn2oL}$). Enteric $CH_4$ emissions ($GHG_e$) are calculated as:

$$GHG_e\left[\frac{\text{kg CO}_2e}{\text{yr}}\right] = \sum\left(DMI\left[\frac{\text{kgDM}}{\text{yr}}\right] \cdot (24.56 - 0.103 \cdot FAT)\left[\frac{\text{kg CH}_4}{\text{kgDM}}\right]\right) \cdot GWP_{CH_4}\left[\frac{\text{kg CO}_2e}{\text{kg CH}_4}\right] \quad \text{EQ 6}$$

where FAT is the amount of additional fat added to each ration. Upstream embedded GHG emissions ($GHG_u$) include the emissions generated when products brought into the control volume are produced "upstream" from the control volume system boundaries, such as purchased corn, fertilizer, fuel, etc. These emissions are calculated as, $$GHG_u\left[\frac{\text{kg CO}_2e}{\text{yr}}\right] = \sum\left(X\left[\frac{X}{\text{yr}}\right] \cdot GHG_X\left[\frac{\text{kg}_{CO2e}}{X}\right]\right) \quad \text{EQ 7}$$

where (X) is the amount of an imported product (e.g., corn, electricity, etc.) and $GHG_X$ is the emissions impact of each product (e.g., 0.47 t $CO_2$e/t corn, 0.176 t $CO_2$e/GJ electricity, etc.) reported in a life-cycle assessment database. On-site emissions ($GHG_O$) are generated from the combustion of diesel fuel and natural gas within the control volume and calculated as:

$$GHG_o\left[\frac{\text{kg CO}_2e}{\text{yr}}\right] = \sum\left(Y\left[\frac{Y}{\text{yr}}\right] \cdot GHG_Y\left[\frac{\text{kg}_{CO2e}}{Y}\right]\right) \quad \text{EQ 8}$$

where (Y) is the amount of fuel (e.g., diesel, natural gas, etc.) and $GHG_Y$ is the emissions impact of each fuel (e.g., 3.24 t $CO_2$e/t diesel, 0.07 t $CO_2$e/GJ natural gas, etc.) reported in a life-cycle assessment database. Soil carbon sequestration ($GHG_S$) is calculated as:

$$GHG_s\left[\frac{\text{kg CO}_2e}{\text{yr}}\right] = -\sum\left(L[ha] \cdot CS\left[\frac{\text{kg}_C}{ha-\text{yr}}\right]\right) \cdot CF\left[\frac{\text{kg CO}_2}{\text{kg C}}\right] \quad \text{EQ 9}$$

where CS is the carbon sequestration rate per land area per year for each type of land used in the model. The total GHG emissions from the herd is calculated as:

$$GHG\left[\frac{\text{kg CO}_2e}{\text{yr}}\right] = GHG_p + GHG_r + GHG_m + GHG_i + GHG_e + GHG_u + GHG_o + GHG_s\left[\frac{\text{kg CO}_2e}{\text{yr}}\right] + GHG_{oth}\left[\frac{\text{kg CO}_2e}{\text{yr}}\right] \quad \text{EQ 10}$$

where $GHG_{oth}$ are other greenhouse gas fluxes. The GHG emissions can allocated between the carcass weight and by-products (hides, tallow, organs, etc.) based on economic allocation (below) or by different allocation methods (mass, energy, etc.) or system expansion with displacement credits. Thus, the GHG emissions per kg of carcass weight (GHG') can be represented as:

$$GHG'\left[\frac{\text{kg CO}_2e}{\text{kg CW}}\right] = \frac{GHG\left[\frac{\text{kg CO}_2e}{\text{yr}}\right] \cdot AF_{CW}[-]}{X_{CW}\left[\frac{\text{kgCW}}{\text{yr}}\right]} \quad \text{EQ 11}$$

where $AF_{CW}$ is the carcass weight allocation factor and $X_{CW}$ is the amount of carcass weight generated each year.

Model equations can characterize the production system, with, for example, equations representing cow-calf models, feeder calf models, finishing models, meat packing models, operations models, etc. The model equations can provide performance results at, for example, global, national, aggregate producer level, groups of animals, or individual animals. In an example cow-calf model, the number of calves born can be represented by:

$$H_{cb}[hd] = H_c \cdot (1 - CowDL) \cdot (PR)[hd] \quad \text{EQ (12)}$$

where $H_C$ is the number of cows (e.g., 100 cows), CowDL is cow death loss rate, and PR is the pregnancy rate. The number of calves surviving to weaning ($H_w$) can be represented by:

$$H_w[hd] = H_{cb} \cdot (1 - \text{CalfDL})[hd] \qquad \text{EQ (13)}$$

where CalfDL is the calf death loss rate before weaning (including birth). It is assumed that half of the calves are heifers and the other half are bulls/steers. The number of calves retained in the herd as replacement heifers ($H_rh$) can be represented by:

$$H_{rh}[hd] = H_c - (H_c \cdot (1 - \text{CowDL}) \cdot (\text{PR}))[hd] \qquad \text{EQ (14)}$$

The number of calves eventually slaughtered ($H_s$) can be represented by:

$$H_s[hd] = (H_w - H_{rg}) \cdot (1 - \text{PWDL})[hd] \qquad \text{EQ (15)}$$

where PWDL is the post-weaning death loss rate. The number of bulls in the herd (Hb) can be represented by:

$$H_b[hd] = H_c \cdot \text{BSR}[hd] \qquad \text{EQ (16)}$$

where BSR is the bull stocking rate (bulls/cows) and the bull breeding life is assumed to be a predetermined year, for example, 4 years.

The amount of pastureland for the cow herd can be determined based on the dry matter intake of the cattle in the model, which can be determined for cow-calf pairs, bulls, replacement heifers, and weaned calves. Rations can be influenced by the genetic parameters in the model, as described below. Rations for cow-calf pairs can be determined for a predetermined number of time periods (e.g., four time periods: early lactation, late lactation, early gestation, and late gestation) using at least one feed ration technique known in the art. One such technique considers pasture, hay, protein supplements, and corn and a baseline average cow weight of, e.g., 1,400 lbs. Bull rations can be determined for a predetermined number of time periods (e.g., two time periods, e.g., summer and winter) consisting of pasture, hay, and protein supplements assuming a baseline average weight of, e.g., 1,600 lbs. Replacement heifers can be assumed to be fed for determined number of days, e.g., 203 days per year (e.g., November 1-April 23) with a ration of hay and protein supplements assuming a baseline average weight during feeding of, e.g., 850 lbs. The amount of land to produce forage ($L_g$) to supply the dry matter can be represented by:

$$L_g = 1.25 \cdot \frac{DM_g}{P} \left[ \frac{\text{lbs/yr}}{\frac{\text{lbs}}{\text{ac} - \text{yr}}} \right] \qquad \text{EQ (17)}$$

where $DM_g$ is the total annual dry matter intake of the herd for pasture and hay consumption (i.e., grass), P is the average productivity (e.g., 1.8 ton/ac-yr (USDA 2019b)), and a factor of safety (1.25) is applied. In one scenario with 100 cows, 379 ac of grassland, for example, can be used for the cow-calf segment. Mineral intake can be estimated for cattle in units of oz/hd-day, for example, depending on body weight for segments of the production pathway.

Continuing with the above example model, weaned calves can be modeled to graze on wheat pasture for a predetermined number of days (e.g., 120 days) and fed hay and protein supplements for a predetermined number of days (e.g., 41 days) for a period of time (e.g., between November 1-April 11). The amount of land for wheat pasture ($L_w$) in this example can be represented by:

$$L_w[ac] = \frac{H_{bg}}{SR} \left[ \frac{hd}{\frac{hd}{ac}} \right] \qquad \text{EQ (18)}$$

where $H_{bg}$ is the number of weaned calves backgrounded on wheat pasture and SR is the stocking rate, e.g., (0.7 hd/ac). Calves can be sent to a feedlot at a predetermined age, e.g., 13 months of age, where they can receive a feedlot ration, such as an example that consists of corn (66%), hay (16%), dried distillers grain (16%), and limestone (<1%). The average daily gain (ADG) and average carcass weight yield (CW) can be determined according to historic data 160 and performance data 139. Manure management can be modeled with a variety of systems (e.g., dry stack solid storage).

In accordance with various embodiments, the model equations can further represent farm practice management data.

In an embodiment, one set of conditions for equation components for farm practice management can include, for example, fertilizer being applied to the grass pasture e.g., (18 lbs DAP/ac-yr, 64 lbs ammonium nitrate/ac-yr, 41 lbs potassium chloride/ac-yr) and wheat pasture, e.g., (27 lbs DAP/ac-yr, 98 lbs ammonium nitrate/ac yr, 62 lbs potassium chloride/ac-yr). Herbicide can be modeled as applied to the grass pasture, e.g., (0.13 gal/ac-yr) and wheat pasture e.g., (0.25 gal/ac-yr), and pesticide e.g., (0.08 gal/ac-yr) and wheat seed e.g., (120 lbs/ac-yr) applied to the wheat pasture. Sub-surface water for cattle to drink can be modeled as consumed at a rate of e.g., 2.5 gal per 100 lbs of body weight for nursing cows and 1.5 gal per 100 lbs of body weight per day for all other cattle.

Continuing further, diesel fuel can be modeled as consumed for the cow-calf segment (e.g., 8 gal/cow-yr), backgrounding (e.g., 7 gal/hd-yr), and the feedlot (e.g., 20 gal/hd-yr). Diesel fuel is also consumed for transporting cattle, e.g., with fuel consumption of 0.2 gallons per mile. Electricity is consumed, e.g., for the cow-calf segment (0.5 MJ/cow-d), backgrounding (0.3 MJ/hd-d), the feedlot (0.8 MJ/hd-day), and the slaughterhouse (172 MJ/hd). Natural gas is consumed, e.g., in the feedlot (2.9 MJ/hd-d) and the slaughterhouse (681 MJ/hd).

In an embodiment, farm management practices can include, post-weaning management, e.g., backgrounding management, direct entry to a feedlot management, grass-finished management, etc.; manure management systems, which can affect methane conversion factor (MCF), direct N2O emissions factor ($NF_D$), and indirect volatile N2O emissions factor ($NF_V$); diet formulations and feed additives that affect enteric CH4 ($GHG_e$) emissions and upstream emissions ($GHG_u$); reducing or replacing inorganic fertilizer with organic fertilizer (e.g., poultry litter), which affects upstream ($GHG_u$) and direct emissions from fertilizer; replacing fossil fuel electricity with renewable electricity (e.g., solar and wind), which affects upstream emissions ($GHG_u$); replacing petroleum fuels with biofuels (e.g., biodiesel, biogas, etc.), which affects upstream ($GHG_u$) and direct emissions ($GHG_o$); replacing high-GHG feedstuffs like DDGS with low-GHG feedstuffs like soymeal, which affects upstream emissions ($GHG_X$); soil carbon sequestration ($GHG_S$); sequestering carbon contained in manure via thermochemical conversion or other methods; reducing the upstream emissions generated from imported products (e.g., reducing emissions from corn production or grid electricity generation), and various other management practices.

In an embodiment, direct-entry-to-feedlot management can include, for example, the situation where weaned calves are sent directly to the feedlot upon weaning and the feedlot ration consists of corn (66%), hay (16%), dried distillers grain (16%), and limestone (<1%). The average daily gain (ADG) and average carcass weight yield (CW) can be determined in accordance with any one of a number of approaches known in the art. The land for the feedlot is assumed to be negligible and manure is managed, e.g., with dry-stack solid storage. As an example, weaned calves can be modeled to enter the feedlot weighing an average of, e.g., 522 lbs and experience an average daily gain of e.g., 3.5 lbs/day for a feeding period of e.g., 233 days, yielding an average slaughter weight of e.g., 1,336 lbs, and an average carcass weight of e.g., 848 lbs.

In an embodiment, grass-finished management can include, for example, the situation where weaned calves are backgrounded on wheat or grass pasture until slaughter. The additional land for grass-finishing can be included in the calculation presented in equation 6, above. The average daily gain (ADG) and average carcass weight yield (CW) can be determined in accordance with any one of a number of approaches known in the art. In an example, grass-finishing can include, e.g., 95 ac of land grazed for 193 days with average daily gain of 1.3 lbs/hd-day, resulting in average slaughter weights of 1,136 lbs, and yielding 653 lb average carcass weights.

In an embodiment, manure management affects emissions from various production segments and for emissions from $CO_2$, $N_2O$, and $CH_4$. $CO_2$ emissions from manure represent a large carbon flux, but are typically carbon-neutral in the overall system as this carbon was initially absorbed by plants during photosynthesis (i.e., biogenic carbon). The manure emissions can be impacted by changes to the manure management system, which can alter model equations. For example, manure management systems can alter the methane conversion factor (MCF), the direct $N_2O$ emissions factor ($NF_D$), and the indirect volatile $N_2O$ emissions factor. For example, one scenario might have a manure management system with pasture manure left in place and dry-stack solid storage in the feedlot. Emissions for different practices (e.g., lagoons) can be calculated on a case-by-case basis by using the corresponding model parameters. In addition, a carbon sequestration credit can be obtained by collecting manure and converting it into a form for long-term storage (e.g., biochar or biogas fuel with subsequent carbon capture and storage).

Adjustment module 126 can be configured to adjust the model equations based on performance data 139, where in various embodiments the models can be adjusted in real time or near real time. For example, a decision algorithm in certain embodiments can be triggered on the input data to select appropriate equations and appropriate input variables for each scenario. In one embodiment, training module 204 can identify the data variables that may be impacted or otherwise associated with select input parameters associated with performance data 139, and can apply adjustments to model equations based on performance data 139.

In an example, the model can be adjusted to account for farm practices management data. For example, the obtained performance data may be used as input data that may be processed to determine expected emissions in accordance with embodiments described herein. This can include, in an example, identifying farm management practices data variables that may affect emissions calculation. For example, training module 204 can identify the data variables that may be impacted by select input parameters and can apply adjustments to model equations based on the historic data 160 and/or performance data 139. That is, adjustment parameters accounting for differences between scenarios can be generated, where the adjustments can be with respect to animal performance or particular farm management practices. For example, industry standard conditions can be determined for a particular breed of animal and/or for particular farm management practices. The industry standard conditions can be adjusted in accordance with embodiments described herein based on genetics and/or farm management practices. Adjustment module 126 applies scaling factors, thresholds, and/or multipliers to model equations to ensure that an appropriate emissions determination is obtained based on farm management data points. The amount and nature of the adjustments may be determined by the farm management data points and/or the data point's likely impact on the determined expected emissions values.

In another example, cattle with greater reproductive efficiency, feed efficiency, and health generate fewer GHG emissions by generating more beef with fewer inputs (and thus fewer emissions). Expected progeny performance data can indicate the relative difference in performance between progeny of animals for a variety of traits, such as birth weight, dry matter intake, yearling height, carcass weight, mature weight, marbling, etc. In turn, these traits can impact the GHG emissions intensity from cattle by influencing the amounts of feeds required for the herd and the amount of manure and carcass weight generated by the herd.

In another example, model adjustments for expected progeny performance data can be based on, for example, adjustment parameters for weaning weight (WnWt), yearling weight (YrWt), calf death loss rate (CalDL), dry matter intake (DMI), average daily grain (ADG), cow death loss rate (CowDL), carcass weight (CarcWt), etc.

In yet another example, adjustment module 126 can be configured to adjust the model equations based on identified farm management data. In one exemplary embodiment, adjustment module 126 applies scaling factors, thresholds, and/or multipliers to model equations to ensure that an appropriate emissions determination is obtained based on performance data.

In yet another example, the model can be dynamically updated based on real-time data 214. For example, sensors 219, 221, and 223 can obtain data associated with one or more animals. The sensors can include, for example, cameras, electronic scales, electronic feeders, temperature sensors, humidity sensors, movement sensors, GPS sensors, body composition sensors, health sensors, ultrasound sensors, gas sensors, feed intake measurement systems, gas sensors or calorimeter, laser-based methane sensors, soil analysis probe sensors, pH sensors, digital thermometers, digital rulers, Biolectric system sensors, ZELP sensors, Herdsy sensors, Allflex RFID sensors, GPI liquid flowmeter, GPI gas flowmeter, Milbank electricity meter, industrial controls, etc. In an embodiment, the animal performance data can include animal consumption, emissions, and behavior data. Animal consumption, emissions, and behavior data can be obtained using one or more sensors. For example, sensors can be used to monitor automatically and continuously the consumption, emissions, and the behavior of individual animals in order to predict and determine a variety of conditions relating to health, feed efficiency, animal welfare, performance, and production efficiency enabling determination of individual animal performance on different rations, response to medications, response to feed supplements, response to minerals and trace minerals, response to growth promoting substances, prediction of carcass quality, and determination of greenhouse gas and manure excretion.

As described, adjustment module 126 can be configured to select different equations for modeling based on historic data 160 and/or performance data 139—such that the algorithm selection is triggered on the input data. The amount and nature of the adjustments may be determined by the performance data and/or the data point's likely impact on the determined expected emissions values.

For example, Table 1 illustrates a list of exemplary adjustment parameters (e.g., model adjustments) along with a range of potential model values and the example values for each parameter. The model adjustments being generated from model equations for weaning weight (WnWt), tearling weight (YrWt), calf death loss rate (CalDL), dry matter intake (DMI), average daily grain (ADG), cow death loss rate (CowDL), carcass weight (CarcWt), etc.

TABLE 1

| Adjustment Parameters | Range | Example Animal A | Example Animal B |
| --- | --- | --- | --- |
| Weaning Weight (lbs) | 379-662 | 515 | 543 |
| Yearling Weight (lbs) | 630-958 | 782 | 834 |
| Calf Death Loss Rate (CalfDL) | 1.5%-8.5% | 4.8% | 3.8% |
| Cow Death Loss Rate (CowDL) | 1.5%-3.5% | 2.3% | 2.2% |
| Dry Matter Intake Factor (DMIF) | 0.69-1.57 | 1.02 | 0.97 |
| Mature Weight Factor (MWF) | 0.91-1.12 | 1.02 | 1.05 |
| Milk Factor (MILKF) | 0.85-1.15 | 1.00 | 1.05 |
| Feedlot ADG (lbs/d) | 3.29-4.2; (GF) 1.33-1.6 | 3.5 | 3.74 |
| Carcass Weight (lbs) | 660-993; (GF) 483-784 | 843 | 879 |
| Pregnancy Rate (PR) | 0.56-1.00 | 0.87 | 0.88 |

Emissions component 212 can apply adjustments to the model equations based on performance data 139. Emissions component 212 is also configured to determine emissions data 222 by one or more selected animals. In an embodiment, emissions data 222 can be obtained by control component 227. Control component 227 is operable to control various appliances 225, including farm appliances and equipment, to alter a farm management task. Appliances 225 can include, for example, a feed formulation appliance, a manure management appliance, a gating system to control a size of a grazing area. Control component 227 can, based on emissions data 222, control appliances 225 to alter the feed formulation, grazing areas, manure management, or other farm management task to achieve emissions goals or thresholds. Accordingly, model 206 can be generated using historic data 160, adjusted based on performance data 139, updated based on real-time data from various sensors (e.g., 219, 221, 223), and then based on emissions data 222, while control component 227 can concurrently or based on some other schedule, alter the feed formulation, grazing areas, manure management, etc. to achieve emissions thresholds. As will be described further below, emissions component 212 models the impact of available characteristics and practices on an animal's lifecycle emissions to generate emissions data.

Figure 3:
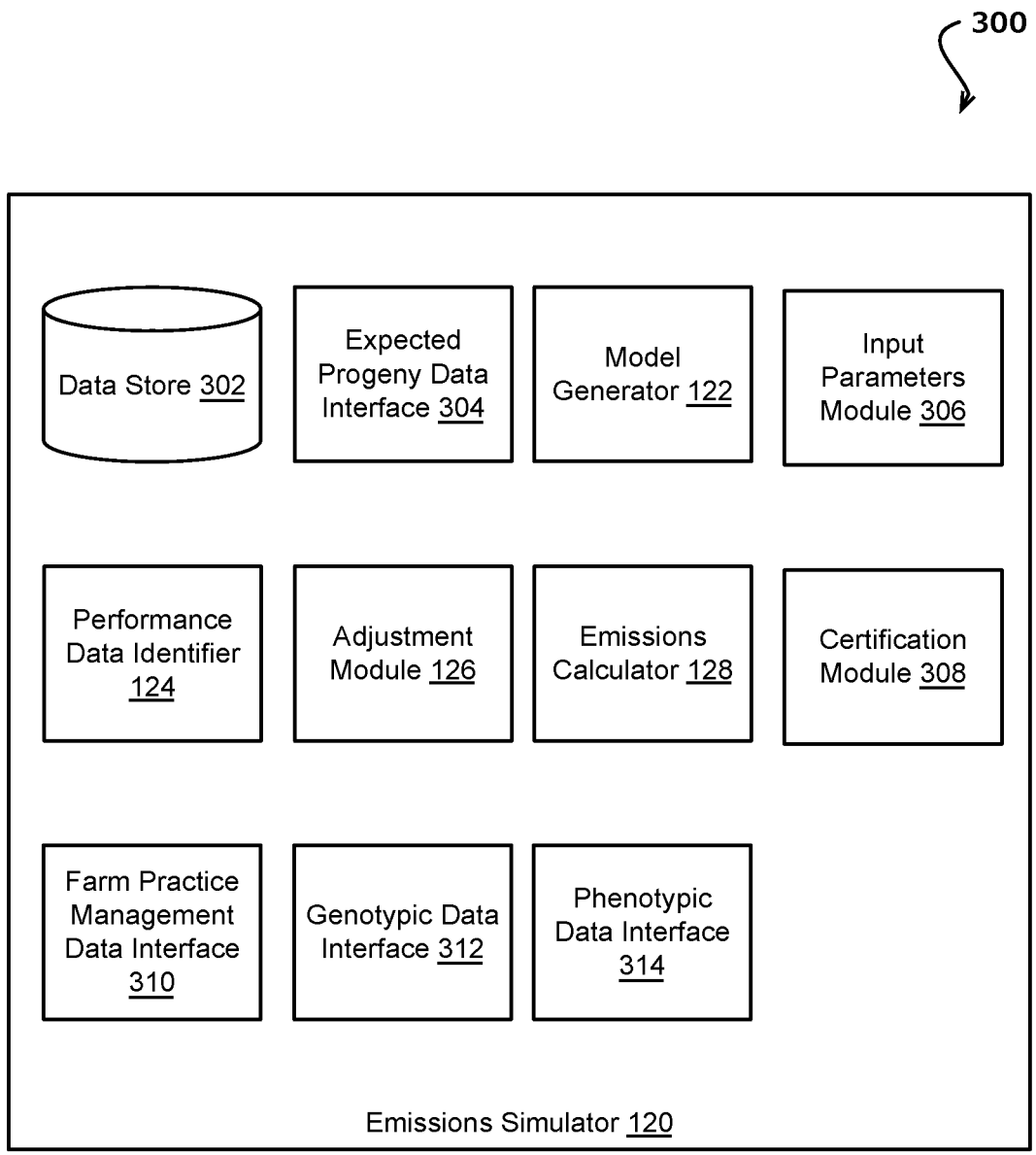
FIG. 3 illustrates the emissions simulator in accordance with various embodiments.

FIG. 3 below illustrates an exemplary embodiment 300 of the emissions simulator 120. As described above, the emissions simulator 120 models the impact of certain characteristics and practices on an animal's lifecycle emissions.

The model output may be comprised of greenhouse gas fluxes, product yields, or other metrics, such as one or more of the following: total lifecycle CO2e emissions, CO2e emissions for part of the lifecycle, CO2e absorbed on farm credit, respiratory CO2e emissions, manure CO2e emissions, CO2e emissions from enteric CH4, CO2e emissions upstream, CO2e emissions from manure N2O, CO2e emissions direct on farm, CO2e emissions from soil N2O, CO2e emissions from manure CH4, CO2e sequestered in soil, CO2e credits, negative CO2e emissions, CO2e sequestration fluxes, carcass weight yield, by-product yields, manure yield, etc. The model may also output different combinations of emissions (e.g., emissions from feedlot only) or the model may output the total emissions for the entire pathway, total methane, and/or total N2O, etc. As used herein, upstream emissions refer to emissions that occur outside of the beef production process, but are "embedded" in energy or materials that are used in the beef production process. Examples include nitrogen fertilizer production: ammonia is produced from natural gas and air offsite and that process causes emissions—but those emissions are attributed to the beef once the farmer purchases the nitrogen fertilizer and uses it on their farm. The same approach can be used for other materials and energy that is imported into the control volume, including, for example, feeds, fuels, seeds, etc.

Although the aforementioned model outputs are detailed herein, other model outputs may be generated as would be apparent to one skilled in the art. The emissions simulator 120 includes data store 302, expected progeny performance data interface 304, model generator 122, input parameters module 306, performance data identifier 124, adjustment module 126, emissions calculator 128, certification module 308 and farm practice management data interface 310, genomics data interface 312, and phenotypic data interface 314. The emissions simulator 120 may also include a control volume analysis. Other generators, parameters, modules and interfaces may be used, as would be readily understood by a person of ordinary skill in the art, without departing from the scope of the embodiments described herein.

The data store 302 is illustrated within the emissions simulator 120 for illustration purposes. It may reside inside or outside the emissions simulator 120, as would be readily understood to a person of ordinary skill in the art. Exemplary data stores 302 include a database for storing data, a database for storing input parameters, a database for storing calculated emissions, a database for storing models. Other databases may be used, as would be readily understood to a person of ordinary skill in the art, without departing from the scope of the embodiments described herein.

The input parameters module 306 utilizes input parameters from selected animal data and other sources to create a model for the input parameters. In an example, one or more input parameters can be added or removed or otherwise selected based on the presence (or absence) of historic emissions and expected emissions data and performance data including farm practices management data, genotpic data, phenotypic data, expected progeny performance data.

A database server or other appropriate component is generally capable of providing an interface for managing data stored in one or more data stores. For example, expected progeny data performance interface 304 communicates with user devices, data store 302, databases, or other repositories or devices to obtain expected progeny data. Farm practice management data interface 310 communicates with farms and/or other relevant databases to obtain farm practice management data. Farm practice management data may be used as input parameters in the adjusted model equations to update expected emissions calculations. Farm practice management data may be comprised of one or more of the following: feeds, fertilizers, manure management data, grazing management data, on-farm energy use data, and water supply/fresh water usage data. Although farms are described herein, ranches, factories, or other locations may interface with embodiments described herein as would be apparent to one skilled in the art.

Genomics data interface 312 interfaces with the genotypic data 140 databases to import data and apply appropriate scaling, thresholding and other calculations that may be relevant or appropriate to incorporate this data into the model generator 122.

The phenotypic data 145 interfaces with the phenotypic data 145 databases to import data and apply appropriate scaling, thresholding, and other calculations that may be relevant or appropriate to incorporate this data into the model generator 122.

Model generator 122, performance data identifier 124, adjustment module 126, and emissions calculator 128, are described above in reference to FIG. 1A.

Certification module 308 assigns one or more certification(s) if the expected emissions are calculated to be above, below, or otherwise satisfy a designated threshold. In one embodiment, the certification module 308 indicates the amount of greenhouse gas emissions that an animal has emitted and/or expected to emit in accordance with the calculation system described herein.

Figure 4:
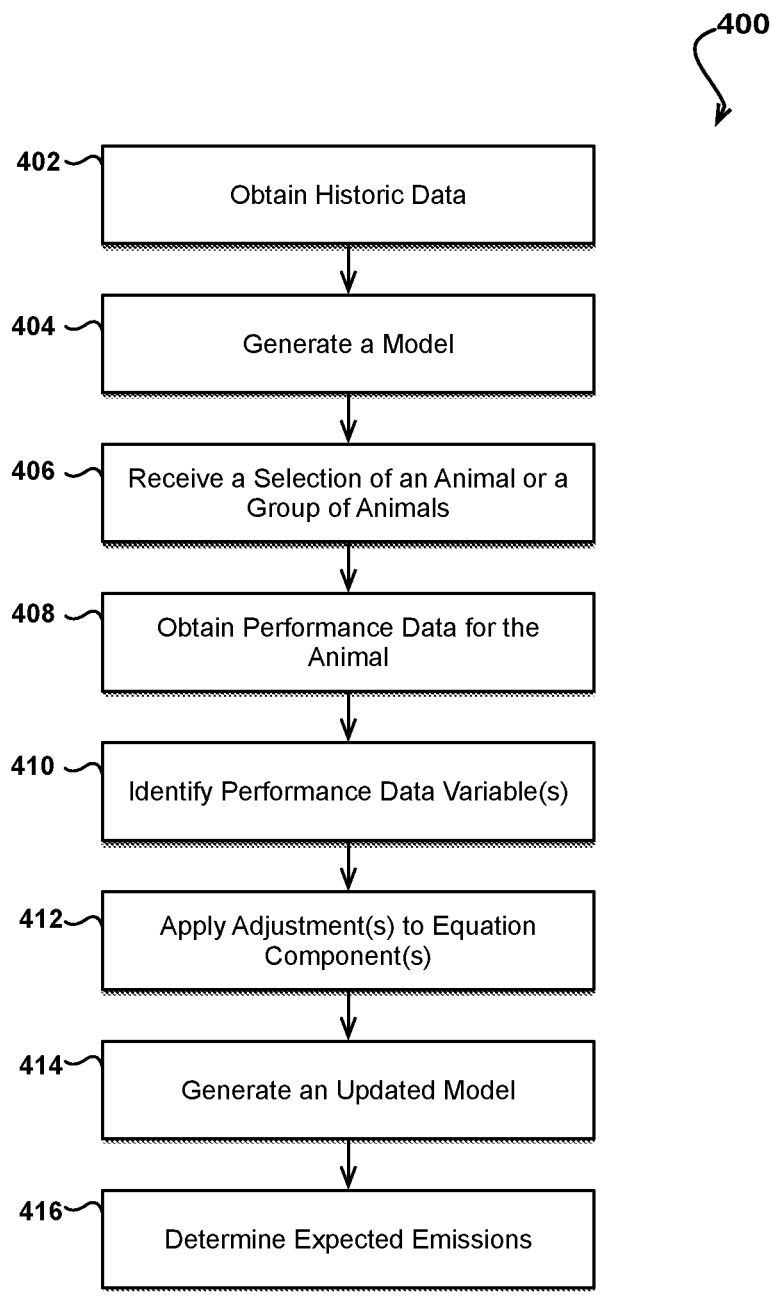
FIG. 4 illustrates an example process for utilizing performance data of animals to estimate emissions for selected animals in accordance with an embodiment.

FIG. 4 below illustrates an exemplary process 400 for estimating emissions for selected animals in accordance with an exemplary embodiment. It should be understood that, for any process discussed herein, there can be additional, fewer, or alternative steps, performed in similar or different orders, or in parallel, within the scope of the various embodiments unless otherwise stated. The process starts by obtaining 402 historic data from a variety of sources such as academic papers, scientific literature, trade publications, experimental data, etc. In one embodiment, the relevant papers may specifically study the effects of various input parameters on emissions. In the same or other embodiments, the relevant papers may study animal characteristics data that may or may not specifically analyze or study animal characteristic data and its direct impact on emissions. For example, the historic data may be comprised of information about different parts of animal lifecycle, including, but not limited to emissions information, economic impact information, etc. In one embodiment, the historic data may be associated with greenhouse gas emissions that an animal may be expected to emit over a period of time, including, for example, over the animal's lifetime. For example, the data may be compiled from academic papers, scientific literature, trade publications, experimental data, etc. In one embodiment, the historic data may be comprised of, for example, dry matter intake (DMI) and its effect on emissions results. In one embodiment, the historic data may be comprised of human and/or machine-readable information that may be processed, as described in more detail below, to perform additional analysis.

The data can be associated with a plurality of input parameters, where individual input parameters may be associated with equation components that cause a threshold level of change in emissions by at least one animal. For example, the relevant papers may specifically study the effects of various input parameters on emissions. This can include, for example, the presentation of one or more equation components modeling the effects of various input parameters on emission. Example input parameters include emissions from, e.g., cow-calf, backgrounding, feedlot, meat packing segments, and provide a measure of lifecycle emissions. The input parameters can be associated with equation components. An equation component can model the impact of certain input parameters on an animal's lifecycle emissions. That is, an equation component can be configured to quantify an amount of emissions based on particular data. For example, electricity and natural gas consumed in the meat packing segment can be represented by at least one equation component. In this example, the equation component can model the impact of electricity and natural gas consumed to the life-cycle emissions of a beef carcass.

The process obtains or identifies one or more equation components to generate 404 a model based on the historic data and/or other data such as performance data including expected progeny performance data, genomic data, phenotypic data, and/or farm practices management data. The generated model may incapsulate the relationship between input parameters, other data points, and their likely impact on greenhouse gas emissions. The model, including the equation components, can quantify an amount of emissions by a group of animals. In particular, the model can quantify the amount of emissions by the group of animals based on available data. The model equations for the model can include, for example, equations representing cow-calf models, feeder calf models, finishing models, meat packing models, operations models, etc. In a specific example, an equation component of the model may quantify how DMI affects emissions output by an animal. The model may include equation components based on historic data in one instance, and/or may be based on a variety of different studies and/or practical correlations that may or may not be present in the historic data. In one embodiment, the equation components may be comprised of historic data, farm practices and protocol data, genotypic data, phenotypic data, etc. that may be received from one or more other database/sources.

A selection of an animal or a group of animals can be received 406. For example, an animal or a group of animals can be associated with a unique identifier (e.g., number, name, etc.). The identifier can comprise, for example, a tag, tattoo, metal ID clip, RFID button, freeze brand, hot brand, microchip, animal recognition technology, DNA testing, pedigree registration, etc.

In this example, the identifier can be associated with data corresponding to the selected animal or group of animals. The data can include, for example, animal characteristic data, performance data, and the like. Performance data can be associated farm management practices, expected progeny performance data, genomics data, phenotypic data, etc.

Based on the selected animal(s), performance data can be obtained 408, which, as described above, may be comprised of historic emissions data, expected progeny performance data, genomic data, phenotypic data, and/or farm practices management data. In an example, performance data associated with farm practices management can include, for example, manure management, grazing management, on farm energy use, water supply (fresh water usage), etc. Performance data associated with genetic characteristics include, for example, weaning weight, yearling weight, calf death loss rate, cow death loss rate, mature weight factor, milk factor, feedlot ADG, carcass weight, pregnancy rate. At least a portion of the data may be obtained in real-time. For example, animal consumption, emissions, and behavior data can be obtained using one or more sensors positioned in accordance with different parts of animal lifecycle. For example, sensors can be used to monitor automatically and continuously the consumption, emissions, and the behavior of individual animals. The sensors can include, for example, cameras, electronic scales, electronic feeders, RFID, temperature sensors, gas sensors, etc.

In an embodiment, the obtained performance data may be used to update the generated model. For example, the obtained performance data may be used as input data that may be processed to determine expected emissions in accordance with embodiments described herein. This can include, for example, identifying 410 performance data variables that may affect emissions calculation. For example, as described, an equation component can model the impact of certain input parameters on an animal's lifecycle emissions. In this situation, an equation component can be configured to quantify an amount of emissions based on certain performance data, such as farm management practice data. For example, the impact of fat into feedlot diets, converting feedlot manure management to daily manure spread rather than solid storage, the use of inorganic fertilizers, replacing all diesel with biodiesel, replacing all electricity with solar power, soil carbon sequestration, emissions-reducing feed additives, etc. can be represented by at least one equation component.

Identifying a data variable associated with at least one equation component of the plurality of equation components can include, for example, identifying data variables associated with equation components determined to impact or otherwise change a level of emissions at least a threshold amount. For example, as described, an equation component can model the impact of certain input parameters on an animal's lifecycle emissions. As such, an equation component can be configured to quantify an amount of emissions based on certain performance data, such as genetic data. In a specific example, an equation component can be configured to quantify an amount of emissions based on reproductive efficiency and feed efficiency. Continuing with this example, with respect to reproductive efficiency, assume calving ease direct (CED) refers to the likelihood that a heifer that has been serviced by a sire will successfully deliver a live calf (the calf being the sire's progeny). In this example, a low calving ease expected progeny performance data may result in a higher death loss, leading to more GHG emissions per kilogram of beef produced by the herd because there is a lower beef yield due to the death loss. Such a relationship can be represented by at least one equation component. Further, a data variable associated with the relationship can be identified.

In another example, calving ease maternal (CEM) is similar to CED, but refers to the calving ease for that sire's daughter (when his daughter has a calf of her own). Such a relationship can be represented by at least one equation component. Further, a data variable associated with the relationship can be identified.

In yet another example, birth weight (BW) can similarly impact live calf birth rate as larger calves are more difficult to birth. Such a relationship can be represented by at least one equation component. Further, a data variable associated with the relationship can be identified.

In yet another example, in the situation that a certain group of animals has better CED, BW, and CEM performance than another group, the result can be lower calf death loss rate and lower cow death loss rate. Such relationships can be represented by at least one equation component. Further, a data variable associated with the relationship can be identified.

In other examples, the following relationships can be represented by at least one equation component, where a data variable associated with the relationship can be identified: the pregnancy rate of a herd given, for example, given heifer pregnancy (HP) as a measure of pregnancy rate in a sire's daughters; scrotal circumference (SC) of a sire impacts conception rates of a sire's sons, but has also has been correlated to reproductive efficiency of his daughters. SC can be considered a threshold trait, meaning there is no impact of SC on herd performance unless SC is abnormally low. Open cows (non-pregnant) produce a lot of emissions and no beef, so reproductive efficiency is an important factor in minimizing GHG emissions of a herd. For example, an animal or group of animals might have a higher SC than another group and a slightly higher HP than the baseline, resulting in a slightly higher predicted pregnancy rate.

With respect to feed efficiency, weaning weight (WW) EPD can be associated with an equation component as a direct impact on the modeled weaning weight of calves. For example, a higher weaning weight results in less time and feed requirements (and therefore lower GHG emissions) to bring an animal from weaning to market conditions (slaughter). Yearling Weight (YW) can be associated with an equation component to quantify the impact on the yearling weight of calves and time-to-slaughter, feed inputs, and GHG emissions in the model. Carcass weight (CW) measures the impacts of carcass yield, where a higher CW directly equates to a greater quantity of beef produced, and thus a lower emissions intensity per lb of beef. Residual average daily gain (RADG) and dry matter intake (DMI) influence feed efficiency and can be associated with an equation component to quantify the impact on the slaughter calves throughout their life, and also on replacement females throughout their breeding life. Milk (MILK) can be associated with an equation component to quantify the impact of the feed intake of cows during lactation periods, where a higher MILK EPD can cause an increased feed intake requirement. Mature weight (MW) can be associated with an equation component to quantify the impact of feed intake in the model as larger cows require more feed.

In another example, expected dry matter intake and/or expected carcass weight, which may ultimately affect the emissions calculations—and, as such, may be identified by the process. As an example, expected progeny performance data can be obtained from breed organizations, such as the American Angus Association, American Herford Association, etc.

The process applies 412 adjustments to identified data variables of equation components to generate 414 an updated model based on identified performance data points, the updated model quantifying an amount of emissions by the selected animal during a lifetime of the animal. In one exemplary embodiment, the process applies scaling factors, thresholds, and/or multipliers to model equation components to ensure that an appropriate emissions calculation is obtained based on performance data. The amount and nature of the adjustments may be calculated by the performance data and/or the data point's likely impact on the calculated expected emissions values. Generally, the adjustments may be calculated based on historical performance data and/or in real time or near real time. For example, adjustment parameters can be determined along with a range of potential model values and the baseline value for each parameter. As described, adjustment parameters can include weaning weight (WnWt), tearling weight (YrWt), calf death loss rate (CalDL), dry matter intake (DMI), average daily grain (ADG), cow death loss rate (CowDL), carcass weight (CarcWt), etc. Additionally, in another exemplary embodiment of the adjustment module 126, thresholds may be applied to the model equations (i.e., positive or negative).

The process determines 416 expected emissions by applying adjusted modeling equations to obtain model output. In one exemplary embodiment, the process determines expected emissions by applying a simulation to create expected probability distributions. In one embodiment, the process determines or models the results many times to figure out the range of possible emissions and the likelihood of the actual value being within the range. One exemplary simulation to calculate expected emissions values may be a Monte Carlo simulation wherein the input is random and many simulations are run in order to determine the probabilities of different outcomes. Other simulations may be used as would be apparent to one skilled in the art.

A variety of different outputs may be calculated, including, but not limited to values for greenhouse gas fluxes, product yields, or other metrics, such as: total lifecycle CO2e emissions, CO2e emissions for part of the lifecycle, CO2e absorbed on farm credit, respiratory CO2e emissions, manure CO2e emissions, CO2e emissions from enteric CH4, CO2e emissions upstream (upstream emissions are emissions that occur outside of the production process, but are "embedded" in energy or materials that are used in the production process), CO2e emissions from manure N2O, CO2e directly emitted on farm, CO2e emissions from soil N2O, CO2e emissions from soil N2O, CO2e emissions from soil N2O, CO2e emissions from manure CH4, CO2e sequestered in soil or other media, CO2e credits, negative CO2e emissions, CO2e sequestration fluxes, carcass weight yield, by-product yields, manure yield, etc. Output metrics can include a variety of measures, such as, but not limited to: kg CO2e/kg carcass weight, kg CO2e/head, etc.

Figure 5:
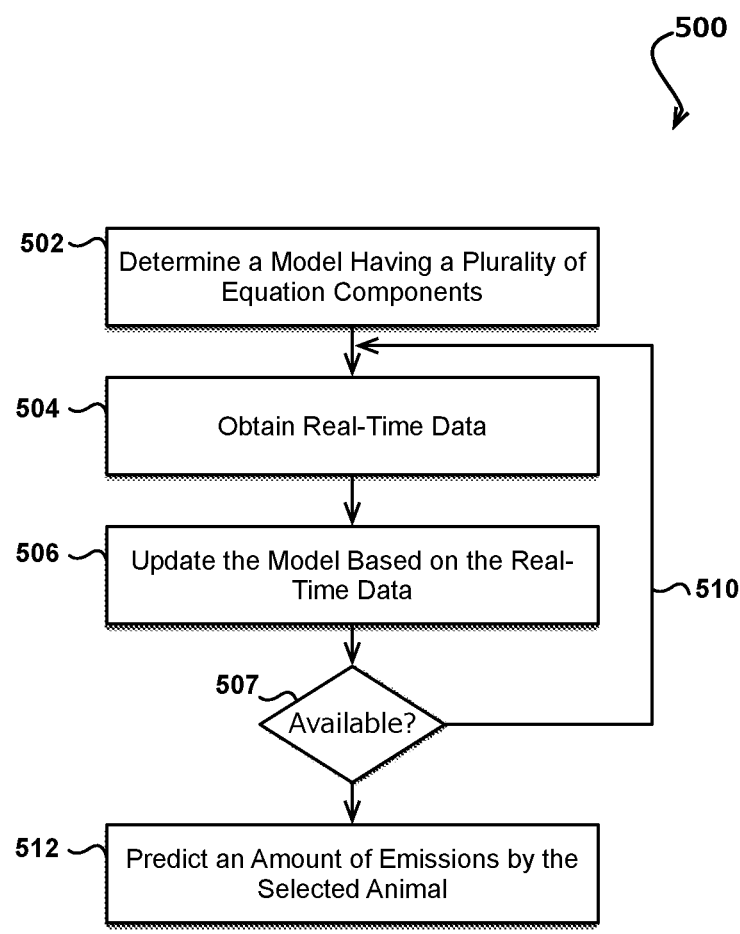
FIG. 5 illustrates an example process for updating a model using real-time data in accordance with various embodiments.

FIG. 5 illustrates an exemplary process 500 for updating a model using real-time data in accordance with various embodiments. In this example, a model comprising a plurality of equation components is determined 502. Real-time data is obtained 504. The real-time data can be obtained using one or more sensors. The sensors can include, for example, image or video recording devices to capture image data, electronic scales to capture weight data, electronic feeders to capture weight data, temperature sensors to capture temperature data, humidity sensors to capture humidity data, gas sensors to capture gas data, movement sensors to capture movement data, GPS data, body composition sensors, health measurements, ultrasound measurements, animal recognition and identification sensors, flowrate sensors, etc. The sensors can obtain data related to animal performance data such as animal consumption data, emissions data, and animal behavior data. For example, the sensors can be used to monitor automatically and continuously the consumption, emissions, and the behavior of individual animals. The data can be used to predict and determine a variety of conditions relating to health, feed efficiency, animal welfare, performance, and production efficiency enabling determination of individual animal performance on different rations, response to medications, response to feed supplements, response to minerals and trace minerals, response to growth promoting substances, prediction of carcass quality, which can be used to determine greenhouse gas and manure excretion.

The equation components can be updated 506 to generate an updated model based on the real-time data. For example, input parameters of the model can be dynamically selected based on available data. This can include, for example, adding or removing one or more input parameters based on the presence (or absence) of the animal performance data. For example, as described, equation components can be identified based on input parameters and the equation components can be adjusted based on real-time data. In this example, the equation components can include equations to weaning weight (WnWt), yearling weight (YrWt), calf death loss rate (CalDL), dry matter intake (DMI), average daily grain (ADG), cow death loss rate (CowDL), carcass weight (CarcWt), etc. A determination can be made 507 whether animal production data is available. In the situation no new animal production data is available, an amount of emissions by a selected animal during the lifetime of the animal can be predicted 512 by evaluating the updated model on the emissions data and the performance data. Additionally or alternatively, the emissions data can be compared to an emissions threshold. In the situation the emissions data represents a level of emissions that does not satisfy the emissions threshold, control instructions including, for example, computer readable instructions, can be generated to control appliances (e.g., farm appliances) to alter the feed formulation, grazing areas, manure management, etc. to achieve emissions goals or thresholds. In the situation new animal behavior data is available, the process can repeat 510 to update the model.

Figure 6:
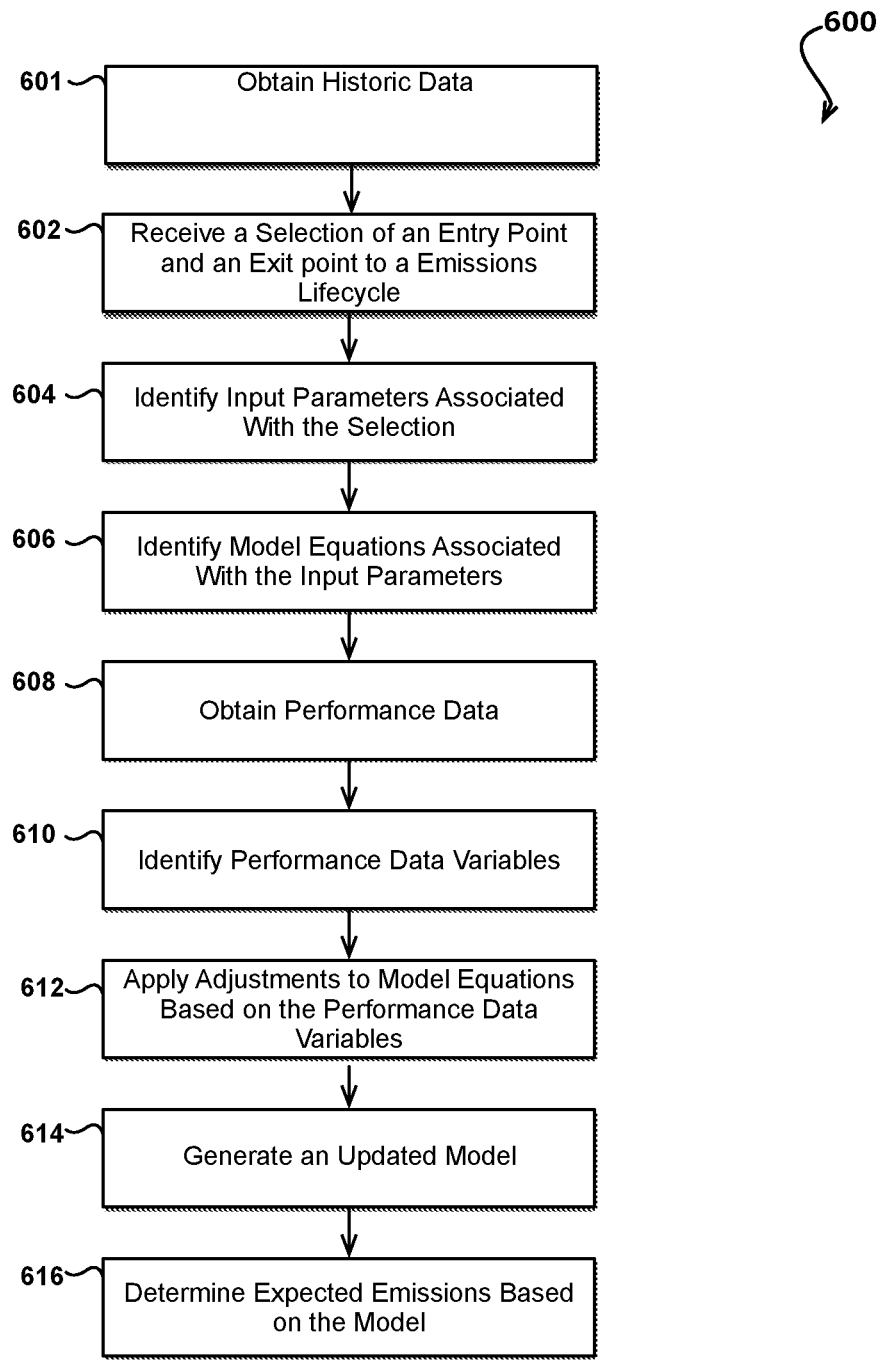
FIG. 6 illustrates an example process for updating a model based on lifecycle emissions pathways in accordance with various embodiments.

In an embodiment, the model may be updated based on an entry point and exit point to the model. For example, FIG. 6 illustrates example 600 for updating a model based on lifecycle emissions pathways in accordance with various embodiments. As described, a model comprises a plurality of model equations. One or more model equations can be associated with a segment of an animal's lifecycle emissions. In an embodiment, an animal's lifecycle emissions can be the amount of emissions by the animal or group of animals during their lifetime or a segment of their lifetime. For example, the animal's lifecycle emissions can include a plurality of lifecycle emissions pathways. An example lifecycle emission pathway can include, a cow-calf lifecycle emission pathway, a backgrounding lifecycle emission pathway, a grass finished lifecycle emission path, etc. Another example lifecycle emission pathway can include cow-calf, backgrounding, and feedlot. Yet another example lifecycle emission pathway can include cow-calf and direct entry to feedlot. The model can output different combinations of emissions (e.g., emissions from segments of pathways such as the feedlot segment) or the model may output the total emissions for any one of the lifecycle emissions pathways.

In one embodiment, the process may include obtaining historic data 601. The historic data may be comprised of the data that is described above in reference to FIG. 4. In another embodiment, the historic data may be derived from the model.

A selection of an entry point and an exit point is received 602. The entry point can correspond to a lifecycle emissions pathway, where the pathway can be associated with one or more model equations. For example, the selection can indicate a lifecycle emissions pathway that considers cow-calf models, backgrounding modes, and grass finished models for determining emissions. In another example, the selection may include an indication of one or more particular segments of pathways. For example, the selection may indicate the grass finished segment. In accordance with embodiments described herein, historic data associated with the selected lifecycle emissions pathway can be obtained and a selection of an animal or a group of animals can be received. Input parameters from historic data associated with the selected lifecycle emissions pathway can be identified 604. Model equations associated with the input parameters can be identified 606. For example, as described herein, the equation components can be based on input parameters that model the impact of certain characteristics on an animal's lifecycle emissions. This can include, in an example, equation components that model the impact of the type of fertilizer being applied to the grass pasture (e.g., organic fertilizer or inorganic fertilizer) on an animal's lifecycle emissions or electricity from fossil fuels versus renewable energy. Performance data, which may be comprised of expected progeny performance data, genotypic data, phenotypic data, farm practices management data, etc. can be obtained 608 and performance data variables that may affect emissions can be identified 610. In accordance with embodiments described herein, adjustments to the model equations can be applied 612 based on the expected progeny performance data. A model can be generated 614. The model includes the model equations. In this example, model generation can include selecting equation components based on the historic data and performance data. In other examples, model generation can include selecting equation components based on the historic data to generate a model, and updating the model based on performance data. In certain embodiments, selecting equation components can be based on historic data and/or performance data. In any situation, a model can be iteratively updated in real-time or other time interval or event detection based on real-time data as described herein.

The model equations can be organized in one or more groups. The one or more groups can be arranged in a hierarchical structure. The structure can include one or more nodes. The path from node to node or node to a base level (i.e., the entry points and exit points) can be considered a lifecycle emission pathway. In this example, the lifecycle emission pathway corresponds to a segment of the lifecycle of one or more animals and can use a particular set of model equations to determine emissions output by the one or more animals. Thereafter, expected emissions for an animal or a group of animals can be determined 616 by evaluating the model. As described, this can include applying the model to obtain a model output, including, but not limited to values for greenhouse gas fluxes, product yields, or other metrics, such as: total lifecycle CO2e emissions, CO2e emissions for part of the lifecycle, CO2e absorbed on farm credit, respiratory CO2e emissions, manure CO2e emissions, CO2e emissions from enteric CH4, CO2e emissions upstream (upstream emissions are emissions that occur outside of the production process, but are "embedded" in energy or materials that are used in the production process), CO2e emissions from manure N2O, CO2e directly emitted on farm, CO2e emissions from soil N2O, CO2e emissions from soil N2O, CO2e emissions from soil N2O, CO2e emissions from manure CH4, CO2e sequestered in soil or other media, CO2e credits, negative CO2e emissions, CO2e sequestration fluxes, carcass weight yield, by-product yields, manure yield, etc. Output metrics can include a variety of measures, such as, but not limited to: kg CO2e/kg carcass weight, kg CO2e/head, etc.

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Figure 7:
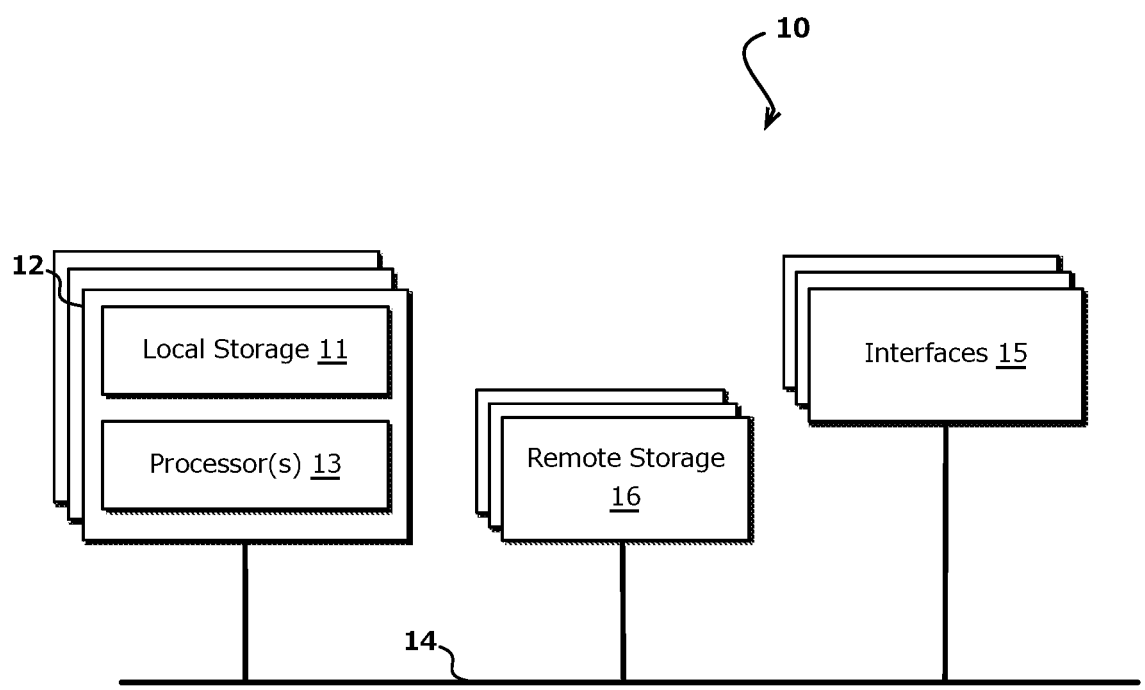
FIG. 7 illustrates an exemplary computing device that can be used in accordance with various embodiments.

Referring now to FIG. 7, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random-access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like.

It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 7 illustrates one specific architecture for a computing device 10 for implementing one or more of the embodiments described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, single processor 13 handles communications as well as routing computations, while in other embodiments a separate dedicated communications processor may be provided. In various embodiments, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 8:
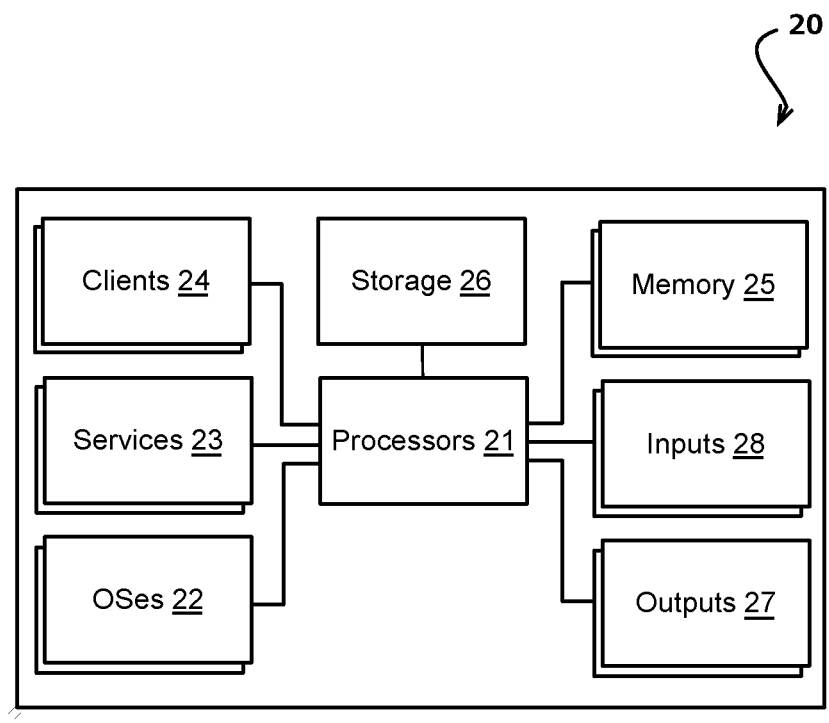
FIG. 8 illustrates an exemplary standalone computing system that can be used in accordance with various embodiments.

In some embodiments, systems may be implemented on a standalone computing system. Referring now to FIG. 8, there is shown a block diagram depicting a typical exemplary architecture of one or more embodiments or components thereof on a standalone computing system. Computing system 20 includes processors 21 that may run software that carry out one or more functions or applications of embodiments, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 22. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described with respect to FIG. 7). Examples of storage devices 26 include flash memory, magnetic hard drive, CD-ROM, and/or the like.

In some embodiments, systems may be implemented on a distributed computing network, such as one having any number of clients and/or servers.

Figure 9:
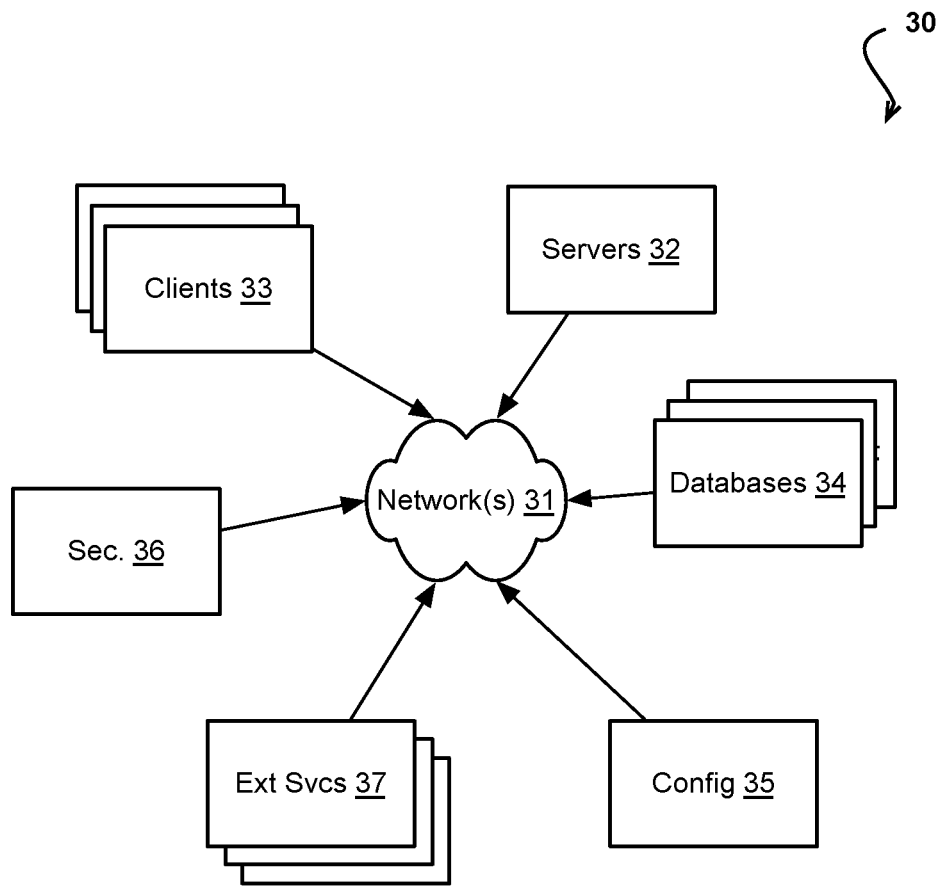
FIG. 9 illustrates an embodiment of the computing architecture that can be used in accordance with various embodiments.

Referring now to FIG. 9, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 8. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises.

In some embodiments, clients 33 or servers 32 (or both) may make use of one or more specialized services or appliances that may be deployed locally or remotely across one or more networks 31. For example, one or more databases 34 may be used or referred to by one or more embodiments. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system.

Unless a specific meaning is specified for a given use of the term "database", it should be construed to mean any of these senses of the word, all of which are understood as a plain meaning of the term "database" by those having ordinary skill in the art.

Similarly, some embodiments may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments without limitation, unless a specific security 36 or configuration system 35 or approach is specifically required by the description of any specific aspect.

Figure 10:
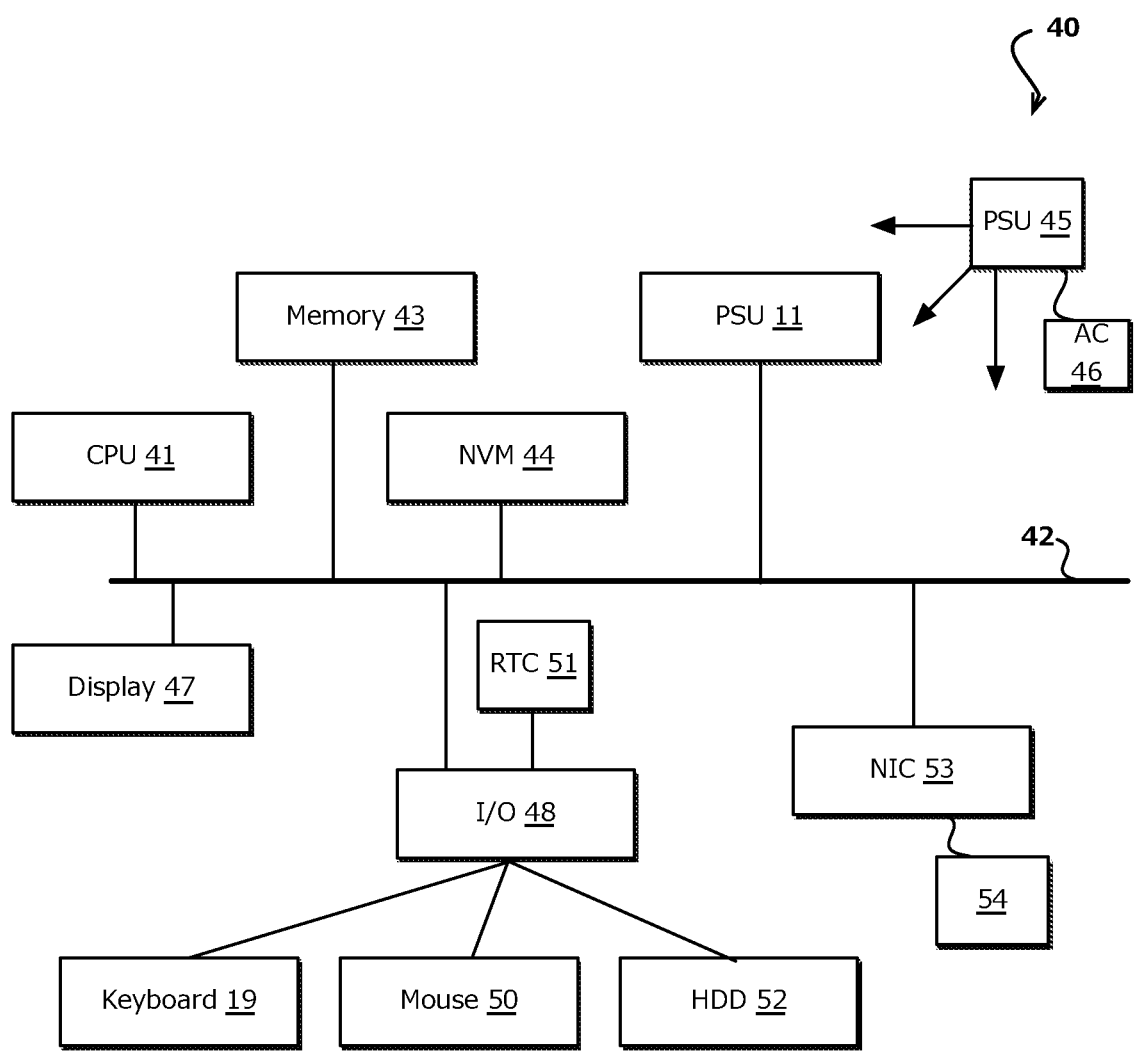
FIG. 10 illustrates an exemplary overview of a computer system that can be used in accordance with various embodiments.

FIG. 10 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48 (including, e.g., keyboard 19, mouse 50, HDD 52, etc.) and network interface card (NIC) 53. I/O unit 48 may, typically, be connected to keyboard 19, pointing device 52, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or." For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A computing system for generating animal-centric emissions models, the computing system comprising:
    a computing device processor; and
    a memory device including instructions that, when executed by the computing device processor, enables the computing system to:
        obtain, by the computing device processor of the computing system, historic animal data from a plurality of different disaggregated sources by scanning an application programming interface (API), the historic animal data associated with a plurality of input parameters of a baseline emissions model;
        identify, by the computing device processor of the computing system, a plurality of equation components corresponding to the plurality of input parameters, individual equation components configured to quantify an amount of emissions;
        generate, by the computing device processor of the computing system, the baseline emissions model comprising the plurality of equation components, the baseline emissions model quantifying an amount of emissions by a group of animals for an emissions lifecycle of the group of animals, the emissions lifecycle including a plurality of potential lifecycle emissions pathways;
        receive a first user selection of an animal associated with the group of animals to identify a selected animal, the animal associated with a unique identifier identifying the selected animal;
        receive a second user selection of a segment of the emissions lifecycle for the selected animal comprising an entry point corresponding to a start date and an exit point corresponding to an end date, the segment associated with one of the plurality of potential lifecycle emissions pathways;
        identify, by the computing device processor of the computing system, equation components associated with the segment;
        obtain in real-time from a database, by the computing device processor of the computing system and at least one sensor of a plurality of sensors monitoring the selected animal, performance data associated with the unique identifier of the selected animal for the segment, wherein the performance data includes expected progeny performance data, expected progeny differences data, genotypic data, phenotypic data, and farm practices management data associated with the selected animal;
        identify, by the computing device processor of the computing system, one or more data variables associated with at least one equation component of the plurality of equation components of the baseline emissions model for the segment based on the performance data;
        apply, by the computing device processor of the computing system, at least one adjustment to the at least one equation component to generate an animal-centric emissions model, the animal-centric emissions model quantifying an amount of emissions by the selected animal during the segment of the emissions lifecycle of the selected animal;
        determine, by the computing device processor of the computing system, an amount of emissions by the selected animal during the segment of the emissions lifecycle of the selected animal by evaluating the animal-centric emissions model on the historic animal data and the performance data; and
        display, for the selected animal associated with the unique identifier, in a graphical user interface one or more views of the amount of emissions during the segment of the emissions lifecycle.

2. The computing system of claim 1, wherein the instructions, whenexecuted by the computing device processor, further enables the computing system to:
    compare the amount of emissions to a threshold level of emissions;
    determine the amount of emissions satisfies the threshold level of emissions; and
    associate at least one certification with the selected animal.

3. The computing system of claim 1, wherein the instructions, when executed by the computing device processor, further enables the computing system to:
obtain additional data from a plurality of sensors;
update one of the historic animal data or the performance data based on the additional data; and
update the animal-centric emissions model based on the additional data.

4. The computing system of claim 1, wherein the instructions, when executed by the computing device processor, further enables the computing system to:
compare the amount of emissions to a threshold level of emissions;
determine the amount of emissions fails to satisfy the threshold level of emissions; and
generate control instructions to control an appliance to alter a farm management task.

5. The computing system of claim 1, wherein the historic animal data specifies input parameters associated with causing at least a threshold amount of change in emissions by at least one animal, and wherein individual input parameters are associated with respective model equations.

6. A computer-implemented method for generating animal-centric emissions models, comprising:
obtaining, by a computing device processor, historic animal data from a plurality of different disaggregated sources by scanning an application programming interface (API), the historic animal data associated with a plurality of input parameters of a baseline emissions model;
identifying, by the computing device processor, a plurality of equation components corresponding to the plurality of input parameters, individual equation components configured to quantify an amount of emissions;
generating, by the computing device processor, the baseline emissions model comprising the plurality of equation components, the baseline emissions model quantifying an amount of emissions by a group of animals for an emissions lifecycle of the group of animals, the emissions lifecycle including a plurality of potential lifecycle emissions pathways;
receiving a first user selection of an animal associated with the group of animals to identify a selected animal, the animal associated with a unique identifier identifying the selected animal;
receiving a second user selection of a segment of the emissions lifecycle for the selected animal comprising an entry point corresponding to a start date and an exit point corresponding to an end date, the segment associated with one of the plurality of potential lifecycle emissions pathways;
identifying, by the computing device processor, equation components associated with the segment;
obtaining in real-time from a database, by the computing device processor and at least one sensor of a plurality of sensors monitoring the selected animal, performance data associated with the unique identifier of the selected animal for the segment, wherein the performance data includes expected progeny performance data, expected progeny differences data, genotypic data, phenotypic data, and farm practices management data associated with the selected animal;
identifying, by the computing device processor, one or more data variables associated with at least one equation component of the plurality of equation components of the baseline emissions model for the segment based on the performance data;
applying, by the computing device processor, at least one adjustment to the at least one equation component to generate an animal-centric emissions model, the animal-centric emissions model quantifying an amount of emissions by the selected animal during the segment of the emissions lifecycle of the selected animal;
determining, by the computing device processor, an amount of emissions by the selected animal during the segment of the emissions lifecycle of the selected animal by evaluating the animal-centric emissions model on the historic animal data and the performance data; and
displaying, for the selected animal associated with the unique identifier, in a graphical user interface one or more views of the amount of emissions during the segment of the emissions lifecycle.

7. The computer-implemented method of claim 6, further comprising:
comparing the amount of emissions to a threshold level of emissions;
determining the amount of emissions satisfies the threshold level of emissions; and
associating at least one certification with the selected animal.

8. The computer-implemented method of claim 6, further comprising:
obtaining additional data from a plurality of sensors;
updating one of the historic animal data or the performance data based on the additional data; and
updating the animal-centric emissions model based on the additional data.

9. The computer-implemented method of claim 6, further comprising:
comparing the amount of emissions to a threshold level of emissions;
determining the amount of emissions fails to satisfy the threshold level of emissions; and
generating control instructions to control an appliance to alter a farm management task.

10. The computer-implemented method of claim 8, wherein the plurality of sensors includes at least one of a camera, a scale, a ruler, a timer, a feeder, a temperature sensor, a pressure sensor, a flow meter, an electrical sensor, a radiation sensor, a gas sensor, a liquid sensor, a humidity sensor, a movement sensor, a global positioning sensor (GPS), a soil composition sensor, a pH sensor, a body composition sensor, a health sensor, animal identification sensor, biomedical sensor, an x-ray sensor, nuclear magnetic resonance sensor, or an ultrasound sensor.

11. The computer-implemented method of claim 6, wherein applying the at least one adjustment further includes:
identifying expected progeny performance data variables associated with the expected progeny performance data, an expected progeny performance data variable being associated with at least one equation component; and
applying adjustments to the expected progeny performance data variables based on the expected progeny performance data.

12. The computer-implemented method of claim 6, wherein applying the at least one adjustment further includes:
identifying farm practices management data variables associated with the farm practices management data, a farm practice management data variable being associated with at least one equation component; and applying adjustments to the farm practices management data variables based on the farm practices management data.

13. The computer-implemented method of claim 6, wherein the historic animal data specifies input parameters associated with causing at least a threshold amount of change in emissions by at least one animal, and wherein individual input parameters are associated with respective model equations.

14. A non-transitory computer readable storage medium storing instructions that, when executed by at least one processor of a computing system, causes the computing system to:
- obtain, by a computing device processor, historic animal data from a plurality of different disaggregated sources by scanning an application programming interface (API), the historic animal data associated with a plurality of input parameters of a baseline emissions model;
- identify, by the computing device processor, a plurality of equation components corresponding to the plurality of input parameters, individual equation components configured to quantify an amount of emissions;
- generate, by the computing device processor, the baseline emissions model comprising the plurality of equation components, the baseline emissions model quantifying an amount of emissions by a group of animals for an emissions lifecycle of the group of animals, the emissions lifecycle including a plurality of potential lifecycle emissions pathways;
- receive a first user selection of an animal associated with the group of animals to identify a selected animal, the animal associated with a unique identifier identifying the selected animal;
- receive a second user selection of a segment of the emissions lifecycle for the selected animal comprising an entry point corresponding to a start date and an exit point corresponding to an end date, the segment associated with one of the plurality of potential lifecycle emissions pathways;
- identify, by the computing device processor, equation components associated with the segment;
- obtain in real-time from a database, by the computing device processor and at least one sensor of a plurality of sensors monitoring the selected animal, performance data associated with the unique identifier of the selected animal for the segment, wherein the performance data includes expected progeny performance data, expected progeny differences data, genotypic data, phenotypic data, and farm practices management data associated with the selected animal;
- identify, by the computing device processor, one or more data variables associated with at least one equation component of the plurality of equation components of the baseline emissions model for the segment based on the performance data;
- apply, by the computing device processor, at least one adjustment to the at least one equation component to generate an animal-centric emissions model, the animal-centric emissions model quantifying an amount of emissions by the selected animal during the segment of the emissions lifecycle of the selected animal;
- determine, by the computing device processor, an amount of emissions by the selected animal during the segment of the emissions lifecycle of the selected animal by evaluating the animal-centric emissions model on the historic animal data and the performance data; and
- display, for the selected animal associated with the unique identifier, in a graphical user interface one or more views of the amount of emissions during the segment of the emissions lifecycle.

15. The non-transitory computer readable storage medium of claim 14, wherein the instructions, when executed by the at least one processor, further enables thecomputing system to:
- compare the amount of emissions to a threshold level of emissions;
- determine the amount of emissions satisfies the threshold level of emissions; and
- associate at least one certification with the selected animal.

16. The non-transitory computer readable storage medium of claim 15, wherein the at least one certification indicates the amount of emissions that the animal has emitted or is expected to emit.

* * * * *